United States Patent
Han et al.

(10) Patent No.: US 9,936,932 B2
(45) Date of Patent: Apr. 10, 2018

(54) X-RAY IMAGING APPARATUS AND METHOD FOR CONTROLLING THE SAME

(71) Applicant: SAMSUNG ELECTRONICS CO., LTD., Suwon-si (KR)

(72) Inventors: Seokmin Han, Seongnam-si (KR); Dong-Goo Kang, Hwaseong-si (KR); Young Hun Sung, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 200 days.

(21) Appl. No.: 14/933,086

(22) Filed: Nov. 5, 2015

(65) Prior Publication Data
US 2016/0157806 A1 Jun. 9, 2016

(30) Foreign Application Priority Data
Dec. 5, 2014 (KR) .......................... 10-2014-0173881

(51) Int. Cl.
G01N 23/04 (2006.01)
A61B 6/00 (2006.01)

(52) U.S. Cl.
CPC ............ *A61B 6/5241* (2013.01); *A61B 6/502* (2013.01); *A61B 6/583* (2013.01); *A61B 6/461* (2013.01); *A61B 6/481* (2013.01); *A61B 6/482* (2013.01)

(58) Field of Classification Search
CPC ........... A61B 6/00; A61B 6/461; A61B 6/481; A61B 6/482; A61B 6/502; A61B 6/583; A61B 6/5241; G06T 2207/30004; G06T 2207/30068; G06T 7/00; G06T 7/0012; G06T 5/00; G06T 5/001; G06T 5/50
USPC ...... 378/54, 62, 56, 98.9; 382/128, 130, 132
See application file for complete search history.

(56) References Cited

U.S. PATENT DOCUMENTS 9,247,913 B2 * 2/2016 Flohr .................... A61B 6/032

* cited by examiner

*Primary Examiner* — Jurie Yun
(74) *Attorney, Agent, or Firm* — Sughrue Mion, PLLC

(57) ABSTRACT

An X-ray imaging apparatus can include an X-ray detector configured to acquire X-ray data by detecting X-rays and an image processor configured to segment a first image generated based on the acquired X-ray data into two or more segmentation regions, to identify one or more materials present in one segmentation region of the two or more segmentation regions, and to acquire an image relating to an object which includes abnormal materials.

20 Claims, 34 Drawing Sheets

Region 1

Region 2

Region 3

Region 4

Region 5

Region 6

Region 7

Region 8

Region 9

X-RAY IMAGING APPARATUS AND METHOD FOR CONTROLLING THE SAME

CROSS-REFERENCE TO RELATED APPLICATION

This application claims priority to Korean Patent Application No. 10-2014-0173881, filed on Dec. 5, 2014 in the Korean Intellectual Property Office, the disclosure of which is incorporated herein by reference.

BACKGROUND

1. Field

Exemplary embodiments relate to an X-ray imaging apparatus and a method for controlling the same.

2. Description of Related Art

X-ray imaging apparatuses are devices used to irradiate an object with X-rays and acquire an image of the interior of the object using X-rays that have passed through the object. The penetration of X-rays varies according to properties of materials constituting the object, and thus, an internal structure of the object may be imaged by detecting the intensity of X-rays that have passed through the object. The X-ray imaging apparatus easily detects the internal structure of the object, and is thus used to detect abnormalities, such as lesions inside a human body in medicine, or to detect the internal structure of an article or a machine part. Further, the X-ray imaging apparatus may for example be used to check the inside of baggage in an airport.

In particular, an X-ray generator generates X-rays and radiates the same to an object, and an X-ray detector detects X-rays passing through the object and transforms the detected X-ray into electrical signals. Since transformation into the electrical signals is performed pixel by pixel, a single X-ray image is obtained by combining the electrical signals corresponding to the respective pixels.

Examples of X-ray imaging apparatuses include a digital radiography (DR) apparatus, a computed tomography (CT) apparatus, a full field digital mammography (FFDM) apparatus, etc.

An example X-ray imaging apparatus includes an X-ray source for emitting X-rays and an X-ray detector for detecting X-rays that have passed through the object. The X-ray imaging apparatus may perform calculations on the basis of an electrical signal generated from an X-ray detector, and may generate a recovered image which can be similar to an ideal image of the inside of the object. In addition, the X-ray imaging apparatus may use the recovered image or a post-processed recovered image as an X-ray image of the object, and may display the resultant X-ray image.

SUMMARY

According to an aspect of one exemplary embodiment, an X-ray imaging apparatus can include an X-ray detector configured to acquire X-ray data by detecting X-rays and an image processor configured to segment a first image generated based on the acquired X-ray data into two or more segmentation regions, to identify one or more materials present in one segmentation region of the two or more segmentation regions, and to acquire an image relating to an object which includes abnormal materials.

The image processor can be further configured to estimate a thickness of the object for the one segmentation region of the two or more segmentation regions.

The image processor can be further configured to select a region of a second image of a phantom based on the estimated thickness of the object.

The image processor can be further configured to generate a mapping image that maps the one segmentation region of the first image to the selected region of the second image based on data regarding the selected region of the second image, wherein the data regarding the selected region of the second image can be data relating to the estimated thickness of the object.

The image processor can be further configured to generate a plurality of mapping images for the two or more segmentation regions of the first image, and to form a recovered image based on the plurality of mapping images.

The image processor can be further configured to identify one or more materials present in the object by displaying the image of the object which includes abnormal materials, and the abnormal material can be a contrast medium injected into the object or abnormal tissues of the object.

The image processor can be further configured to generate an emphasized image which includes an indication of a region of the first image mapped to the contrast medium or the abnormal tissues.

The image processor can be further configured to determine a number of the two or more segmentation regions and shapes of the two or more segmentation regions based on the object.

The first image can include a dual energy X-ray image of the object.

The second image can include a dual energy X-ray image of the phantom.

The apparatus can further include a storage unit configured to store data regarding a region of the second image corresponding to a thickness of an object.

According to an aspect of another exemplary embodiment, a method for controlling an X-ray imaging apparatus can include acquiring X-ray data by detecting X-rays, and segmenting a first image generated based on the acquired X-ray data into two or more segmentation regions, identifying one or more materials present in one segmentation region of the two or more segmentation regions, and acquiring an image regarding an object which includes abnormal materials.

The method can further include estimating a thickness of an object for the one segmentation region of the two or more segmentation regions.

The method can further include selecting a region of a second image of a phantom based on the estimated thickness of the object.

The method can further include generating a mapping image that maps the one segmentation region of the first image to the selected region of the second image based on data regarding the selected region of the second image, wherein the data regarding the selected region of the second image is data relating to the estimated thickness of the object.

The method can further include generating a plurality of mapping images for the two or more segmentation regions of the first image, and forming a recovered image based on the plurality of mapping images.

The method can further include determining the number of the two or more segmentation regions and the shapes of the two or more segmentation regions based on the object.

The first image can include a dual energy X-ray image of the object.

The second image can include a dual energy X-ray image of the phantom.

The method can further include storing data regarding a region of the second image corresponding to a thickness of an object.

According to an aspect of yet another exemplary embodiment, a system for X-ray imaging, can include an X-ray detector configured to acquire X-ray data by detecting x-rays; and an image processor configured to process the acquired X-ray data, wherein the image processor generates a first image of an object based on X-ray data acquired from the object, divides the first image into a plurality of segmentation regions including at least a first segmentation region and a second segmentation region, generates a second image of a phantom based on X-ray data acquired from the phantom, divides the second image into a plurality of phantom calibration regions including at least a first phantom calibration region and a second phantom calibration region, selects the first phantom calibration region for the first segmentation region and the second phantom calibration region for the second segmentation region, generates a first mapping image by mapping the first segmentation region to the first phantom calibration region and a second mapping image by mapping the second segmentation region to the second phantom calibration region, identifies abnormal material in the object based on the first mapping image and the second mapping image, and generates an emphasized image which includes an indication of a region of the first image mapped to the abnormal material based on the identification of abnormal material.

The image processor also estimates a first thickness of the object within the first segmentation region and a second thickness of the object within the second segmentation region, and selects the first phantom calibration region for the first segmentation region based on the first estimated thickness and the second phantom calibration region for the second segmentation region based on the second estimated thickness.

BRIEF DESCRIPTION OF THE DRAWINGS

These and/or other aspects of the exemplary embodiments will become apparent and more readily appreciated from the following description of the exemplary embodiments, taken in conjunction with the accompanying drawings of which.

DETAILED DESCRIPTION

Figure 1A:
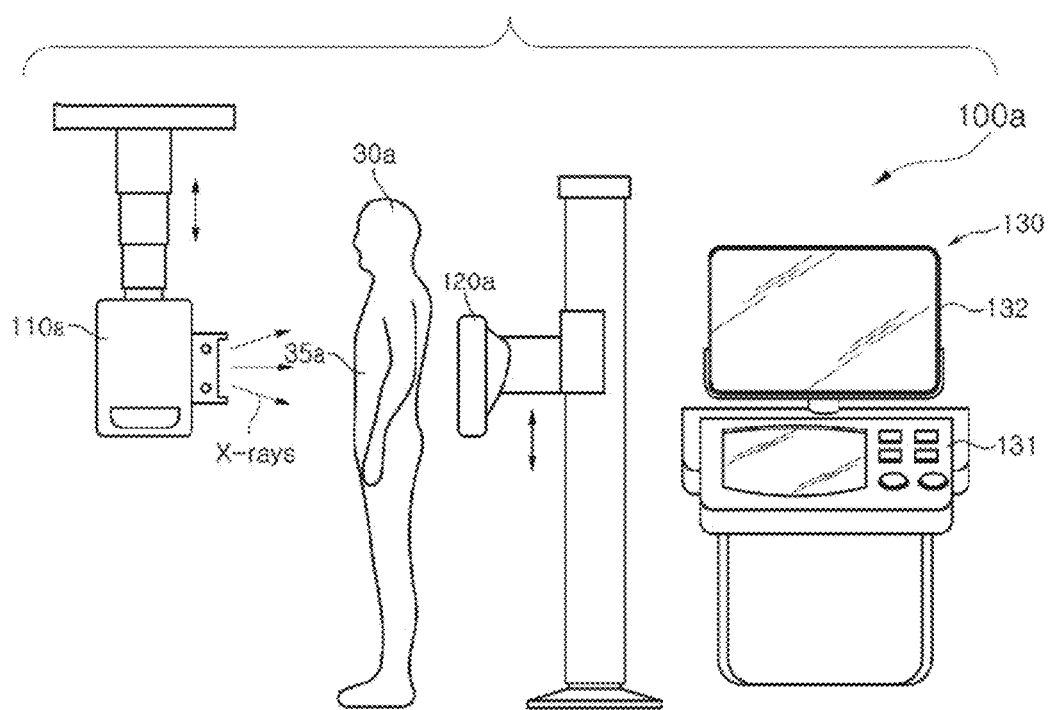
FIG. 1A is a view illustrating an external appearance of an X-ray imaging apparatus according to an exemplary embodiment.

Advantages and features of exemplary embodiments and a method of achieving the advantages and features of the exemplary embodiments will be clearly understood from the description below in conjunction with the accompanying drawings. Reference will now be made in detail to exemplary embodiments, examples of which are illustrated in the accompanying drawings, wherein like reference numerals refer to like or similar elements throughout.

An X-ray imaging apparatus and a method for controlling the same according to the embodiments will hereinafter be described with reference to the attached drawings. Wherever possible, the same reference numbers are used throughout the drawings to refer to the same or like portions.

The X-ray imaging apparatus according to exemplary embodiments may include at least one of an X-ray imaging apparatus, an X-ray fluoroscopy apparatus, a computed tomography (CT) scanner, etc.

An X-ray imaging apparatus may have various structures or imaging schemes depending on a part to be imaged, the type of an X-ray image, or the purpose of imaging. For example, there exist a general X-ray imaging apparatus to image the chest, arms, legs, etc., an X-ray imaging apparatus using mammography to image the breast, an X-ray imaging apparatus using fluoroscopy, an X-ray imaging apparatus using angiography, an X-ray imaging apparatus for cardiography, an X-ray imaging apparatus using tomography, etc. An X-ray imaging apparatus according to an exemplary embodiment may be one or a combination of the above-mentioned X-ray imaging apparatuses. For convenience of description and better understanding of the exemplary embodiments, it is assumed that the medical image forming apparatus is an X-ray imaging apparatus or a mammography-based X-ray imaging apparatus. The term "X-ray image" is an image of an object acquired using X-rays. The object may be organs of a human body, fetus, animals, metal, nonmetal, or some parts thereof. For example, the object may include organs of the human body (e.g., a liver, a heart, a uterus, a brain, a breast, an abdomen) or blood vessels. In addition, the object may include a phantom. The phantom may indicate a material having a volume approximate to both a density of a living thing and an effective atomic number.

The term "users" may indicate medical experts, for example, doctors, nurses, medial technologists, medial image specialists, ultrasonic inspectors, etc. In addition, the term "users" may also indicate technicians who repair medical devices. However, the scope or spirit of the exemplary embodiments is not limited thereto.

FIG. 1A is a view illustrating the external appearance of an X-ray imaging apparatus according to an exemplary embodiment.

Referring to FIG. 1A, the general X-ray imaging apparatus 100a may include an X-ray generator 110a, an X-ray detector 120a, and a host device 130.

The X-ray generator 110a generates X-rays and radiates X-rays to a subject 30a so as to obtain an X-ray image of an object 35a to be imaged.

Here, the subject 30a may be a human body, an animal body or anything else whose inner structure can be imaged by the X-ray imaging apparatus 100a.

The object 35a may indicate a part of the subject 30a whose inner structure is detected using the X-ray imaging apparatus 100a, i.e., a part to be imaged by X-rays. Accordingly, the object 35a may be the head, chest, arms, legs or the like.

The X-ray generator 110a may hang from the ceiling. The X-ray generator 110a moves in a vertical direction so that the position of the X-ray generator 110a may correspond to the position of the object 35a. In this case, the X-ray generator 100a moves in a vertical direction, i.e., along the direction from the ceiling to the floor, and also moves in a horizontal direction.

The X-ray detector 120a is located opposite the X-ray generator 110a with respect to object 35a, so that the X-ray detector 120a may detect X-rays that emitted from the X-ray generator 110a and passed through the object 35a. In addition, the X-ray detector 120a may convert the detected X-rays into an electrical signal.

The X-ray detector 120a may be movable in a vertical direction of a stand. In the same manner as in the X-ray generator 110a, the X-ray detector 120a may be movable in response to the position of the object 35a along the vertical direction of the stand.

In another exemplary embodiment, the X-ray imaging apparatus may be constituted such that the subject 30a is laid on a table, the X-ray generator 110a is mounted to the ceiling so as to move in the length direction of the table, and the X-ray detection unit 120a is mounted inside the table so as to move in the length direction of the table. However, the X-ray generator and the X-ray detector may also be arranged to be movable in various ways.

Referring to FIG. 1A, the X-ray imaging apparatus may include a host device 130 that displays an X-ray image and performs data processing using X-ray data obtained from the X-ray generator 110a and the X-ray detector 120a.

The host device 130 may include an input unit 131 through which a user can input a command and a display 132 to display an X-ray image, thereby providing a user interface.

The input unit 131 may include at least one of a switch, a keyboard, a track ball, a touchscreen, a touchpad, a button, and a stick-type manipulator, without being limited thereto.

The display 132 may be a cathode ray tube (CRT), a liquid crystal display (LCD), a light emitting diode (LED) or the like, without being limited thereto.

Figure 1B:
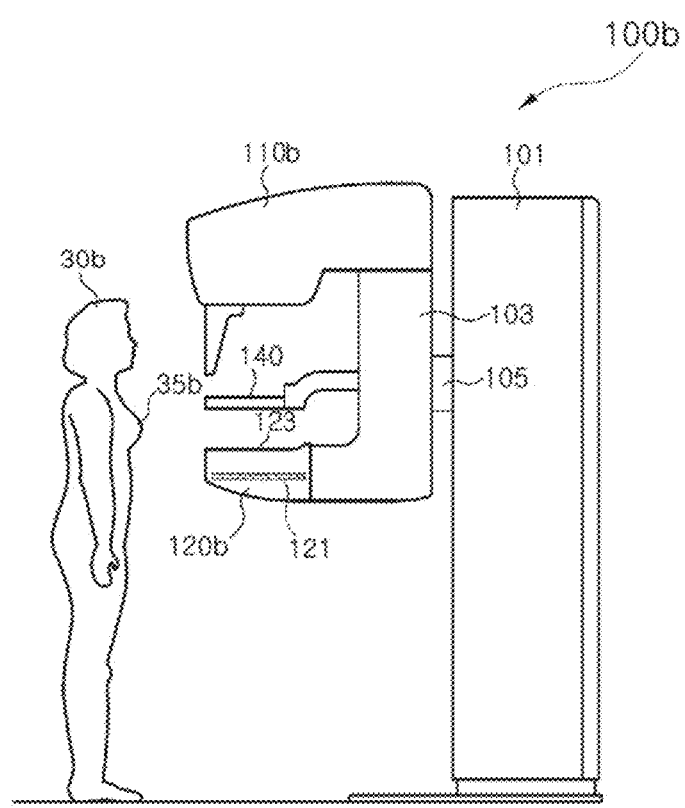
FIG. 1B is a view illustrating an external appearance of an X-ray imaging apparatus used in mammography according to an exemplary embodiment.

FIG. 1B is a view illustrating an external appearance of an example X-ray imaging apparatus based on mammography according to an exemplary embodiment.

Referring to FIG. 1B, the X-ray imaging apparatus 100b based on mammography may broadly include an X-ray generator 110b, an X-ray detector 120b, and a pressing paddle 140.

The X-ray detector 110b and the X-ray detector 120b may be connected to the frame 103 so that the X-ray generator 110b and the X-ray detector 120b face each other. The frame 103 may be connected to the main body 101 through the arm 105. The arm 105 moves in a vertical direction so that the height of the arm 105 is adjusted to the height of the subject or the arm 105 rotates by a predetermined angle. As a result, the X-ray imaging apparatus 100b may also obtain a tomographic image or a three-dimensional (3D) image of the object.

The X-ray imaging apparatus 100b may capture an image of the breast, and may generate an X-ray image of the breast. For example, the object 35b may be the breast. In this case, the object 35b may indicate a target site of the subject 30b to be diagnosed using the X-ray imaging apparatus 100b, and the subject 30b may be a living organism such as a human.

During X-ray imaging of the breast, the breast indicated by object 35b is located between the X-ray generator 110b and the X-ray detector 120b, and X-rays having passed through the breast from among X-rays emitted from the X-ray generator 110b may be detected by the X-ray detector 120b.

The X-ray detector 120b may serve as a support or table for supporting the breast, and may also be referred to as a bucky. The X-ray detector 120b may include an X-ray detector 121 for detecting X-rays and a breast contacting unit 123 contacting the breast. The breast contacting unit 123 may be formed of a material having superior X-ray transmissivity. For example, the breast contacting unit 123 may be formed of a carbon sheet.

The X-ray imaging apparatus for imaging the breast may include structural characteristics different from those of a general X-ray imaging apparatus due to characteristics of the breast tissues. For example, one of the structural characteristics may be the pressing paddle 140 for pressing the breast as shown in FIG. 1B.

For example, if the breast is placed on the breast contacting unit 123 of the X-ray detector 120b, the user moves the pressing paddle 140 in a vertical direction by manipulating the input unit, so that the breast placed on the breast contacting unit 123 can be pressed.

The reason why the breast is imaged after being pressed by the pressing paddle 140 is to reduce an X-ray dose on the breast as well as to obtain a high-definition X-ray image of the breast.

Figure 2:
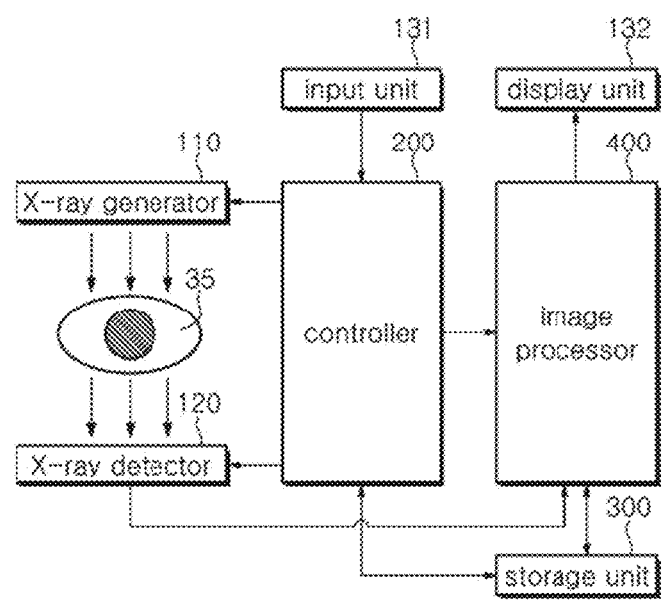
FIG. 2 is a control block diagram illustrating an X-ray imaging apparatus according to an exemplary embodiment.

FIG. 2 is a control block diagram illustrating an X-ray imaging apparatus according to an exemplary embodiment.

Referring to FIG. 2, the X-ray imaging apparatus 100 may include an input unit 131, an X-ray generator 110, an X-ray detector 120, a controller 200, a storage unit 300, an image processor 400, and a display 132.

The X-ray generator 110 may generate X-rays and emit the X-rays to the object 35, and may include an X-ray tube to generate X-rays.

The X-ray generator 110 may emit X-rays to the object 35 according to a predetermined capture region (that is, within a predetermined Field Of View; FOV), or may emit X-rays to only some parts of the object 35. In other words, if all of the object 35 is within the capture region FOV, the X-ray generator 100 emits X-rays to all of the object 35. In contrast, if only some regions of the object 35 are within the capture region FOV, the X-ray generator 110 may emit X-rays only to the corresponding region, resulting in reduction of X-ray exposure dose.

The X-ray detector 120 may detect X-rays that pass through the object 35 after being emitted from the X-ray generator 110, or may detect X-rays that are directly applied without passing through the object 35.

The X-ray detector 120 may convert the detected X-rays into an electrical signal. In this case, the converted electrical signal may hereinafter be referred to as an X-ray signal. The X-ray signal obtained by the X-ray detector 120 may be stored in the storage unit 300 or applied to the image processor 400.

The X-ray detection unit 120 can be classified by an element constitution type, a method of converting the detected X-ray into electrical signals and a method of obtaining the electrical signals.

The X-ray detection unit 120 may be classified into a detection unit constituted by a monolithic type element and a detection unit constituted by hybrid-type elements according to the element constitution type.

The X-ray detection unit of a monolithic type element is constituted such that both a part configured to detect X-rays and generate electrical signals and a part configured to read and process the electrical signals are configured as the same semiconductor or manufactured by the same process. For example, a charge coupled device (CCD) or a complementary metal oxide semiconductor (CMOS), which is a light receiving element, can be used.

The X-ray detection unit of hybrid-type elements can be constituted such that a part configured to detect X-rays and generate electrical signals and a part configured to read and process the electrical signals are configured as different elements from each other or manufactured by different processes. For example, X-rays can be detected by a light receiving element, such as a photodiode, CCD, CdZnTe or the like, and the electrical signals can be read and processed by a CMOS readout integrated circuit (ROIC). Alternatively, X-rays may be detected by a strip detector, and the electrical signals may be read and processed by a CMOS ROIC. In another alternative, an a-Si or a-Se flat panel system is used.

The X-ray detection unit 120 may also be classified according to a method of transforming X-rays into electrical signals, for example as using a direct transformation mode or an indirect transformation mode.

In the direct transformation mode, if X-rays are radiated, electron-hole pairs are temporarily generated in the light receiving element, and the electrons move to the anode and the holes move to the cathode by an electric field applied to both ends of the light receiving element. The X-ray detection unit 120 transforms such movement into electrical signals. In this case, a material used for the light receiving element may include a-Se, CdZnTe, $HgI_2$, $PbI_2$ or the like.

In the indirect transformation mode, a scintillator is provided between the light receiving element and the X-ray generator 110. X-rays radiated from the X-ray generator 110 react with the scintillator and photons having a wavelength of visible light are emitted. The light receiving element detects the photons and transforms the same into electrical signals. In this case, a material used for the light receiving element may include a-Si or the like, and the scintillator may be embodied as a thin-film type GADOX scintillator, or a micro-column type or needle structured type CSI (T1) scintillator.

Additionally, the X-ray detection unit 120 may be classified according to a method of obtaining electrical signals, for example as a charge integration mode in which charges are stored for a certain time and then signals are obtained, or as a photon counting mode in which photons having energy greater than threshold energy are counted whenever signals are generated by a single X-ray photon.

Figure 3:
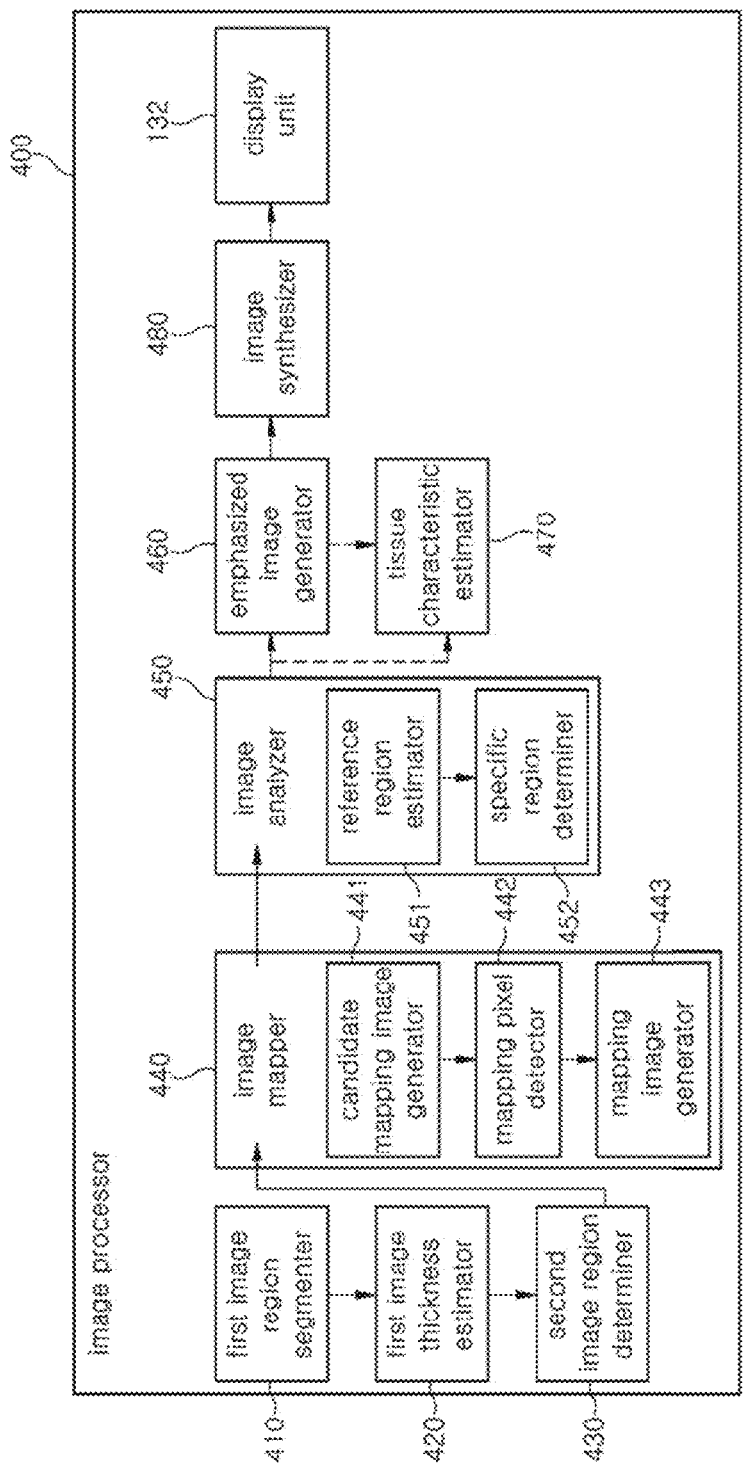
FIG. 3 is a control block diagram illustrating an image processor according to an exemplary embodiment.

FIG. 3 is a control block diagram illustrating an image processor according to an exemplary embodiment.

Referring to FIG. 3, the image processor 400 may include a first image region segmenter 410, a first image thickness estimator 420, a second image region determiner 430, an image mapper 440, an image analyzer 450, an emphasized image generator 460, a tissue characteristic estimator 470, and an image synthesizer 480. In addition, the image mapper 440 may include a candidate mapping image generator 441, a mapping pixel detector 442, and a mapping image generator 443. The image analyzer 450 may include a reference region estimator 451 and a specific region determiner 452.

The constituent elements of the image processor 400 may correspond to one or more processors. Here, the processor may be an array of plural logic gates, or may be a combination of a universal microprocessor and a memory in which a program to be executed by the microprocessor is stored. In addition, those skilled in the art of the present embodiment will understand that the image processor 400 may be other types of hardware.

In association with the control method of the above-mentioned image processor 400, the X-ray imaging apparatus and a method for controlling the same according to an embodiment will hereinafter be described in detail.

The X-ray imaging apparatus and a method for controlling the same according to the embodiments may generate and display an angiographic image of abnormal tissues present in the human body using an angiography contrast medium. Here, the abnormal tissues may include cancer cells, tumors, etc.

The following embodiments will hereinafter be described using the X-ray imaging apparatus for imaging the breast or the mammographic images as an example. However, the scope or spirit of the exemplary embodiments is not limited to the breast imaging or mammography, and it should be noted that the embodiments can also be applied to general X-ray imaging apparatuses and other regions of the human body.

A first image is a first radiation image of multiple energy bands of a local region of a human body. For convenience of description and better understanding of the exemplary embodiments, although the local region of the human body may be breast tissues, the scope or spirit of the exemplary embodiments is not limited thereto. In addition, a second image may be a second radiation image of a thickness variable phantom. The phantom may be a material having a volume approximate to both a density of a living thing and an effective atomic number.

For the X-ray imaging method, a dual energy X-ray imaging method can be used. The dual energy X-ray imaging method sequentially emits X-rays of first energy and X-rays of second energy to the object so as to acquire a dual energy X-ray image.

For example, according to the dual energy X-ray imaging method, the intensity and amount of second energy are adjusted using brightness information of an X-ray image of first energy of the object, so that a correct X-ray image in which characteristics of the object are reflected can be obtained and a disease or lesions can be correctly diagnosed. Generally, the first-energy X-ray and the second-energy X-ray may use radiation images of two energy bands corresponding to a radiation image of a high-energy band and a radiation image of a low-energy band, respectively. For convenience of description and better understanding of the exemplary embodiments, the first-energy X-ray and the second-energy X-ray may correspond to a red-wavelength energy band and a blue-wavelength energy band.

As described above, the dual energy X-ray imaging method compares a captured image of the object contained in the human body and a phantom capture image with all pixels so as to examine or inspect tissues or the like of the object.

In this case, an abnormal material having an energy band exceeding two kinds of energy bands must be determined. When the captured image is compared with all pixels, if the amount of abnormal materials is very small or the region of abnormal materials is very small in size, or if the existing range of two energy bands is very large in size, it is difficult to clearly determine the existing part of abnormal materials. Therefore, an X-ray imaging apparatus and the method for controlling the same according to the exemplary embodiments can segment an image of the object into a plurality of sub-images according to respective images, and can decide the region of a phantom corresponding to each thickness by estimating a thickness of each sub-region of the object, so that an image corresponding to the abnormal material can be discriminated by mapping pixels to the corresponding region. If the angiography contrast medium is applied to the human body, abnormal materials may correspond to a part having the contrast medium. For example, in the case of breast tissues, the abnormal material may include abnormal tissues such as tumors.

The constituent materials of the breast tissues may include adipose tissues and glandular tissues. The respective tissues of each person may have different densities. Therefore, the thickness variable phantom model is needed to reflect the above-mentioned density variation. In the embodiment, the constituent materials may include two kinds of materials, i.e., adipose tissues and glandular tissues. The respective tissues may use a thickness variable phantom in which respective tissues have successive thicknesses. The thickness variable phantom may include various kinds of thickness variable phantoms well known to those skilled in the art.

Normal tissue constructing the breast tissues of the human body may include adipose tissue and glandular tissue as described above. Abnormal tissues such as tumors may be mixed with the breast tissue. In the above-mentioned case, radiation images of multiple energy bands may include a total of three abnormal materials, e.g., adipose tissue, glandular tissue, tumors. If abnormal tissues, such as tumors, having components different from two kinds of tissues (i.e., adipose tissue and glandular tissue) are contained in the object, the mapping distribution of abnormal tissues is different from the mapping distribution of major tissues (adipose tissue and glandular tissue) due to influence of an attenuation coefficient or the like, according to the mapping distribution of radiation images of the breast tissues and the thickness variable phantom. Therefore, the exemplary embodiments aim to discriminate abnormal tissues having distribution different from those of two major components, so that the abnormal tissues can be emphasized and displayed.

Figure 4:
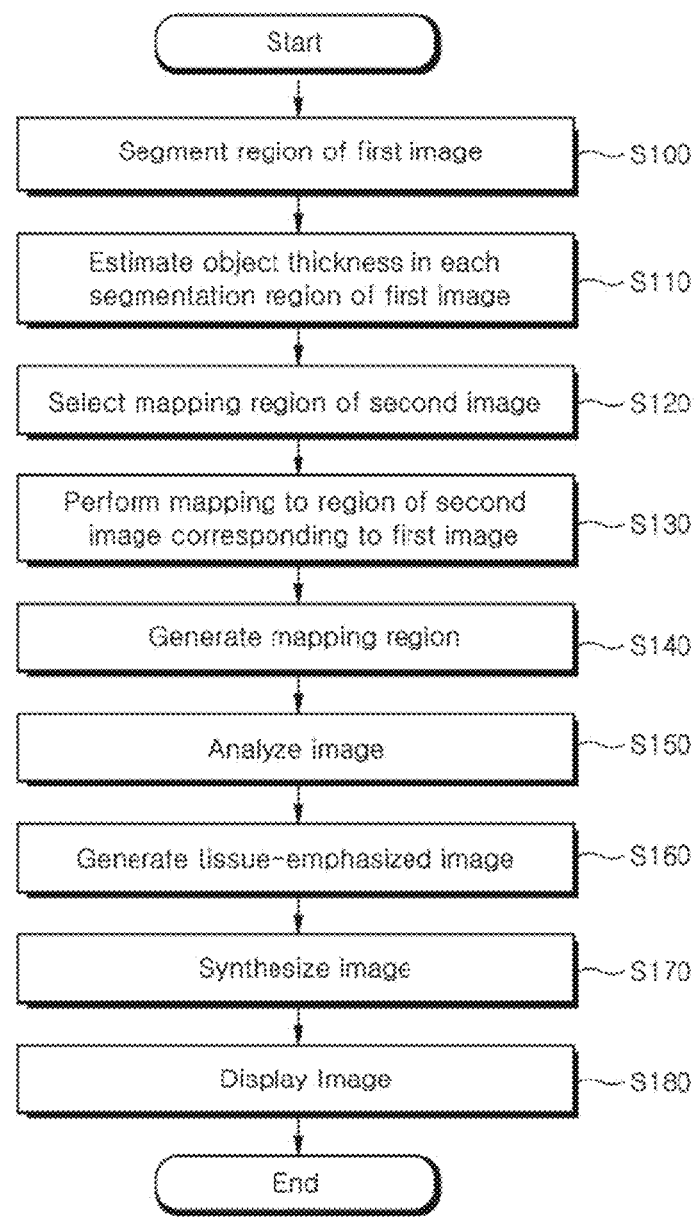
FIG. 4 is a flowchart illustrating a method for controlling an X-ray imaging apparatus according to an exemplary embodiment.

FIG. 4 is a flowchart illustrating a method for controlling an X-ray imaging apparatus according to an exemplary embodiment.

The X-ray imaging apparatus and the method for controlling the same according to embodiments will hereinafter be described with reference to FIGS. 3, and 5 to 14 on the basis of the flowchart of FIG. 4.

Referring to FIGS. 3 and 4, the first image region segmenter 410 may perform image segmentation of a first image in operation S100. As described above, the first image is a first radiation image of multiple energy bands of a local region of the object.

In accordance with the embodiment, the first image indicates that a local image of the object indicates the breast tissues. In order to map the first image to a radiation image of a thickness variable phantom for each segmentation region, image segmentation of the first image is performed. In accordance with the image segmentation, the number of segmentation regions and the shape of a section may be changed according to categories of the object, data regarding the number of segmentation regions or the shape of a section is prestored according to categories of the target, and image segmentation may also be performed on the basis of the prestored data.

Figure 5A:
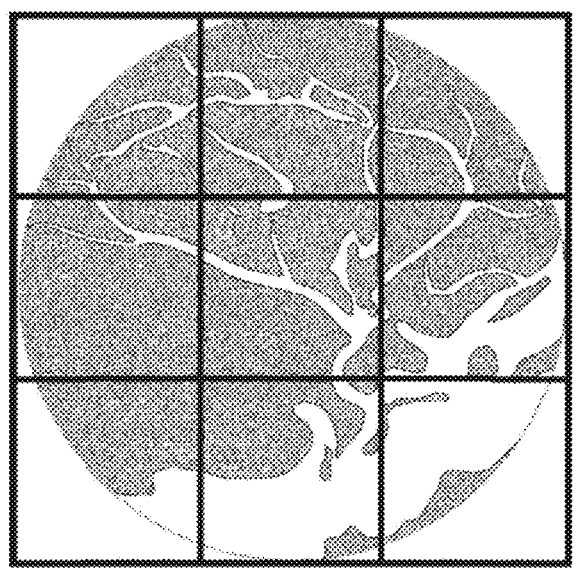
FIGS. 5A-5B are views illustrating a region in which a first image will be segmented into a plurality of images according to an exemplary embodiment.
Figure 5B:
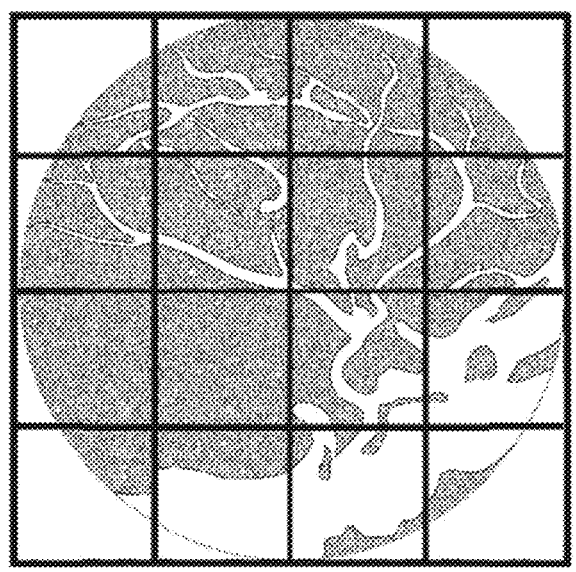

FIGS. 5A and 5B are views illustrating a region in which a first image will be segmented into a plurality of images according to an exemplary embodiment.

Referring to FIGS. 5A and 5B, FIG. 5A shows an example first image that is segmented into 9 regions, and FIG. 5B shows an example first image that is segmented into 16 regions. For convenience of description and better understanding of the exemplary embodiments, although FIG. 5A shows a first image that is segmented into 9 regions and FIG. 5B shows a first image that is segmented into 16 regions, the number of segmentation regions and the shape and size of segmentation regions may be changed according to categories of the object, or for any other desired reason. However, the scope or spirit of the exemplary embodiments is not limited to the section segmentation method of FIGS. 5A and 5B.

FIGS. 6A-6I are conceptual diagrams illustrating a method for segmenting a first image into a plurality of segmentation images so as to estimate a thickness of an object per segmentation image.

Referring to FIGS. 6A-6I, if the first image is segmented into 9 regions, the 9 regions may be denoted by Regions 1 to 9. FIGS. 6A-6I show that a first image of the breast tissues is segmented into 9 regions, and a method for estimating a thickness of the breast tissue for each region will hereinafter be described in detail.

Referring back to FIG. 4, the first image thickness estimator 420 may estimate a thickness of the object in each segmentation region of the first image in operation S110.

The estimation of the thickness of the object in each segmentation region of the first image may include measuring a thickness of the segmentation region of the first image. As shown in FIGS. 6A-6I, respective sections of the first image segmented into 9 regions may be displayed, and a thickness of the object for each section is estimated. The object including the breast tissue is a part of the human body, and all regions of the object are irregular. The object includes an aggregate of segments having different thicknesses.

For example, in association with the radiation image (e.g., an X-ray image), the relationship between the incident intensity and the transmitted intensity will hereinafter be described. Transmissivity of X-rays is changed according to category and density of the object and the energy band of X-rays. The incident intensity and the transmitted intensity can be represented by the following equation $$I(E)=I_0(E)e^{-\mu(E)\rho x} \quad \text{[Equation 1]}$$

In Equation 1, I(E) may denote the transmitted intensity, and $I_0(E)$ may denote the incident intensity. $\mu(E)$ may denote a mass attenuation coefficient at the energy band (E), $\rho$ may denote the density of a subject, and x may denote a thickness of a subject. The above-mentioned principle may indicate the Beer-Lambert Law, and is obvious to those skilled in the art.

Generally, there is a difference in X-ray attenuation coefficients according to the material categories and the energy bands. For example, respective energy bands may have different X-ray attenuation coefficients, for example, adipose tissue, glandular tissue, Infiltrating Ductal Carcinoma (IDC), etc.

In the case of using radiation of two or more multi-energy bands, images ($I_1, I_2, I_3, \ldots, I_n$, where n is an energy band) for respective energy bands may be represented by the following equation 2.

$$\begin{pmatrix} I_1 \\ I_2 \\ \vdots \\ I_N \end{pmatrix} = \begin{pmatrix} \int_E w_1(E)\left(\exp\left(-\sum_i C_i \mu_i(E)\right)\right) dE \\ \int_E w_2(E)\left(\exp\left(-\sum_i C_i \mu_i(E)\right)\right) dE \\ \vdots \\ \int_E w_N(E)\left(\exp\left(-\sum_i C_i \mu_i(E)\right)\right) dE \end{pmatrix} \quad \text{[Equation 2]}$$

In this case, $w_n$ may denote the X-ray incident intensity of the energy band (n), and is denoted by $C_i=\int_L c_i(r)dr$ which indicates material density projections at a position vector (r). In Equation 2, if images ($I_1, I_2, I_3, \ldots, I_n$, where n is an energy band) of respective energy bands are obtained, the material density projections ($C_i$) are obtained from the images of respective energy bands, so that materials of the local region tissues of the object can be separated from each other.

The number of attenuation bases of the constituent material of the local region tissues of the object is set to 2. That is, the attenuation basis is photoelectric absorption and Compton scattering. If a maximum of 2 materials are mixed, respective materials can be isolated from each other. A first radiation image of multiple energy bands may be approximated to the model shown in the following equation 3.

$$I_{tr}(E)=I_{init}(E)e^{-\mu_f t_f - \mu_g t_g} \quad \text{[Equation 3]}$$

In Equation 3, $I_{tr}(E)$ may denote the intensity of X-rays having passed through the object, $I_{init}(E)$ may denote the intensity of X-rays before passing through the object to be imaged, $\mu_f$ may denote an attenuation coefficient of the adipose tissue, $t_f$ may denote a thickness of adipose tissue, $\mu_g$ may denote an attenuation coefficient of glandular tissue, and $t_g$ may denote a thickness of glandular tissue. As can be seen from Equation 3, the breast tissue to be imaged may include a combination of adipose tissue and glandular tissue.

In Equation 3, the attenuation coefficients ($\mu_f, \mu_g$) are well known to those skilled in the art, and unknown variables are $t_f$ and $t_g$. Therefore, assuming that an X-ray image (such as a first radiation image of multi-energy bands) having different tube voltages can be captured and imaged, it may be possible to recognize thicknesses of respective materials.

When estimating a thickness of the breast tissue corresponding to the first image, a thickness variable phantom in which respective tissues have successive thicknesses may be used. Without the necessity of imaging the phantom images associated with all densities, the ratio of materials contained in the local region of the object and the thickness of a material can be estimated using only one radiation image associated with the thickness variable phantom. However, the scope or spirit of the exemplary embodiments is not limited thereto, and the embodiment may also be applied to a thickness variable phantom or other kinds of phantoms having similar characteristics. A mapping image is formed by mapping the first image to the second image, and a thickness of the breast tissue can be estimated from the mapping result in which the thickness of the breast tissue is mapped to the thickness variable phantom. The method for estimating the thickness of the breast tissue in association with the image mapping will hereinafter be described in detail.

In addition to the above-mentioned method, the thickness of the breast tissue of the object may be estimated according to the region of a first image. The thickness of the breast tissue may be directly measured from the captured first image, and the thickness for each region may be estimated on the basis of predetermined data.

The first image thickness estimator 420 may measure a thickness for each region on the basis of the previously measured and stored data, and the user may input thickness data for each region. Referring to FIGS. 6A-6I, Region 1 may have a thickness of 9 cm, and Region 2 may have a thickness of 11 cm. In association with a plurality of regions having irregular thicknesses capable of being measured, an average thickness may also be measured on the basis of a volume shape of each region.

Referring to FIGS. 3 and 4, the second image region determiner 430 may decide or select the mapping region of the second image on the basis of a thickness of the object in response to each region of the estimated first image in operation S120. The second image is a radiation image associated with the thickness variable phantom, and the mapping region of the second image is determined in such a manner that the second image can be mapped to the first image.

FIGS. 7A-7I are views illustrating the mapping regions displayed on a second image of a thickness variable phantom according to an exemplary embodiment.

Figure 6A:
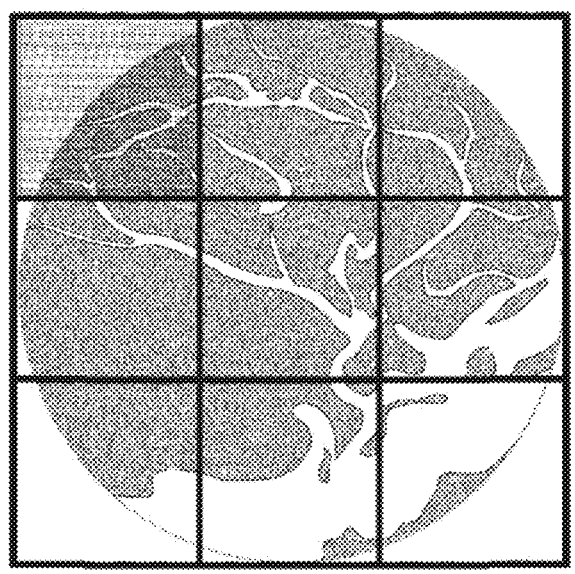
FIGS. 6A-6I are conceptual diagrams illustrating a method for segmenting a first image into a plurality of segmentation images so as to estimate a thickness of an object per segmentation image.
Figure 6B:
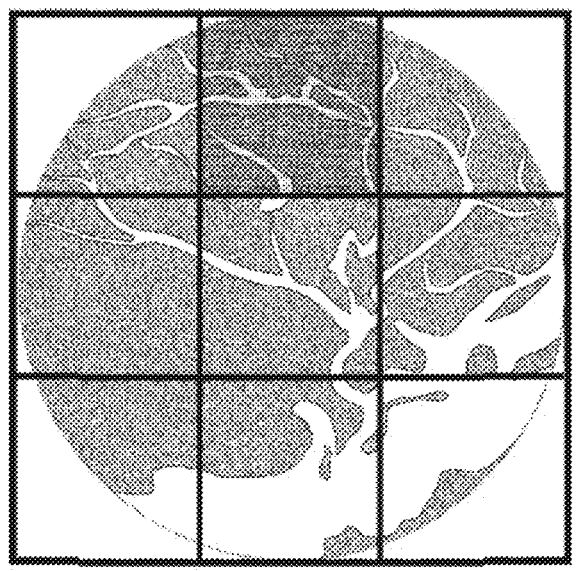
Figure 6C:
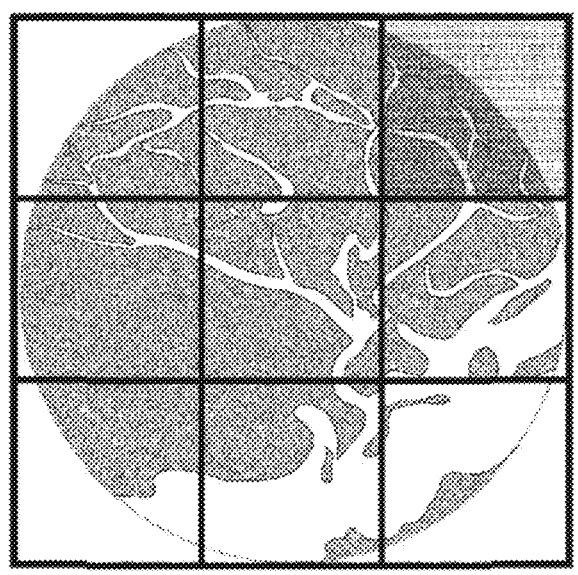
Figure 6D:
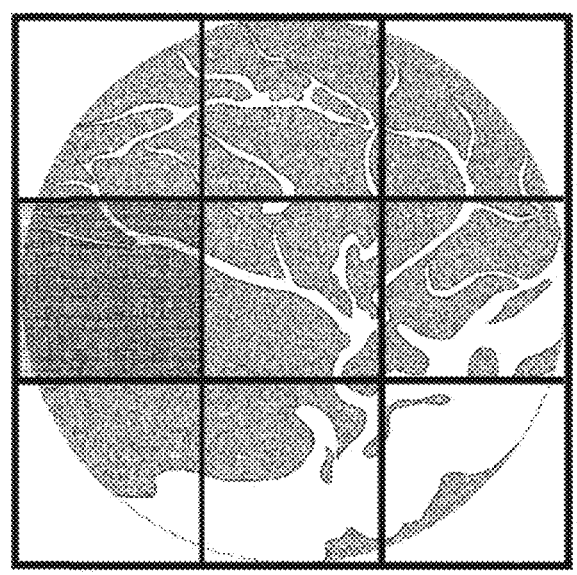
Figure 6E:
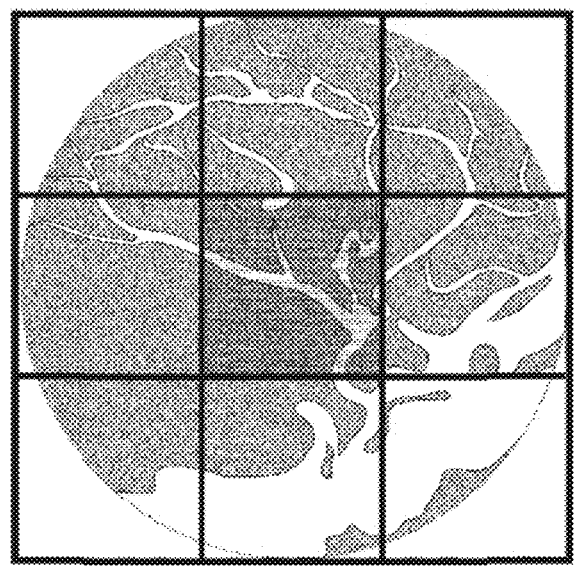
Figure 6F:
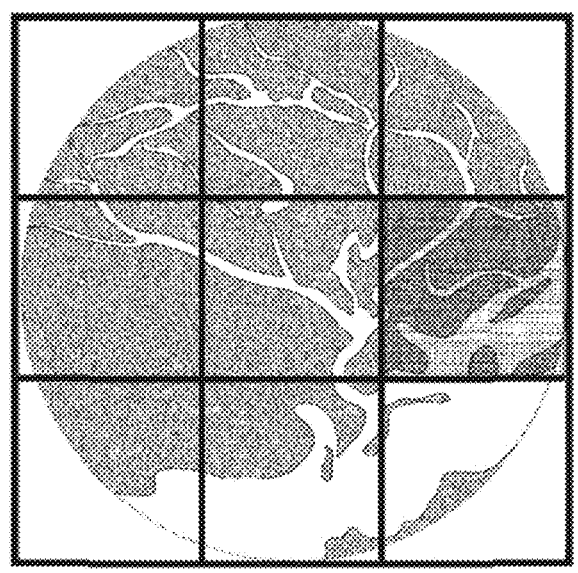
Figure 6G:
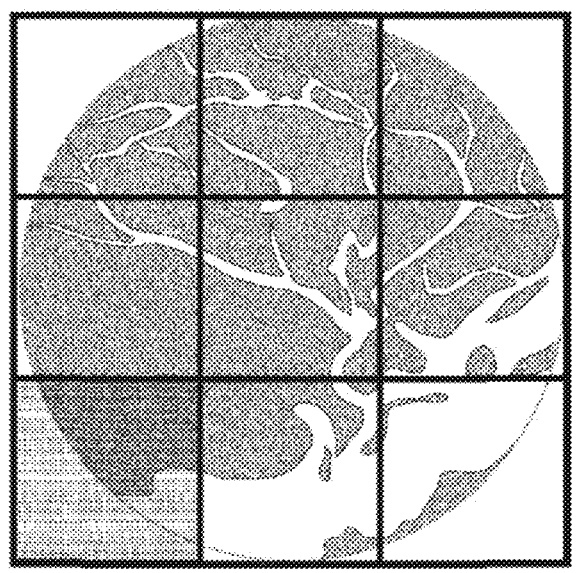
Figure 6H:
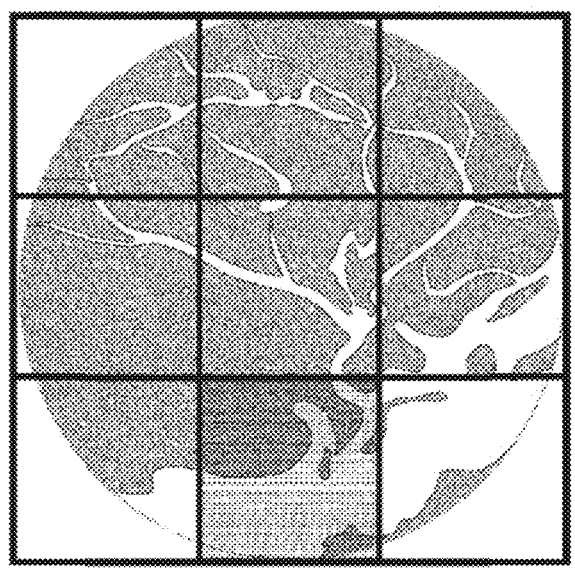
Figure 6I:
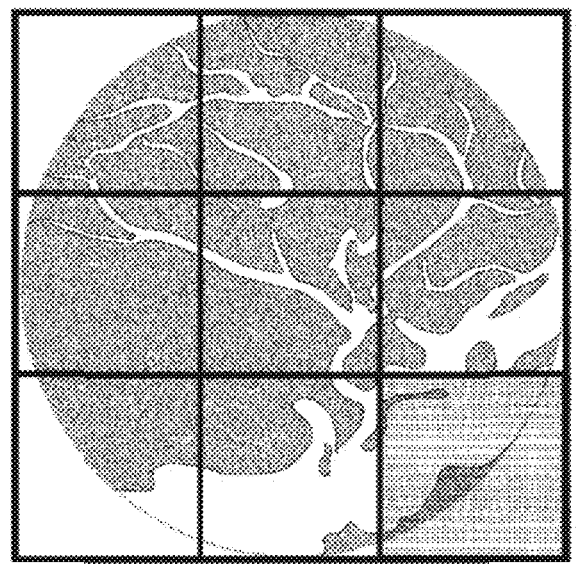
Figure 7A:
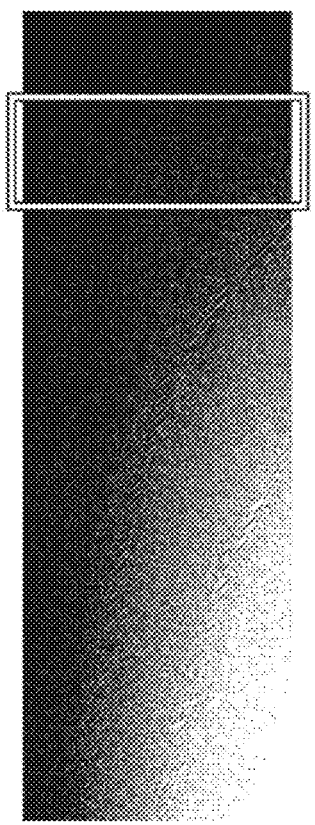
FIGS. 7A-7I are views illustrating the mapping regions displayed on a second image of a thickness variable phantom according to an exemplary embodiment.
Figure 7B:
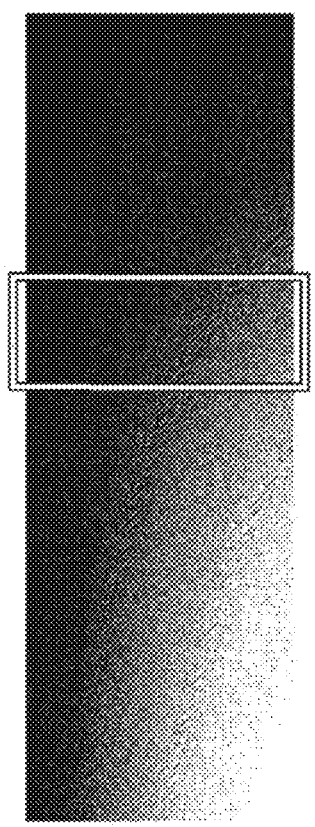
Figure 7C:
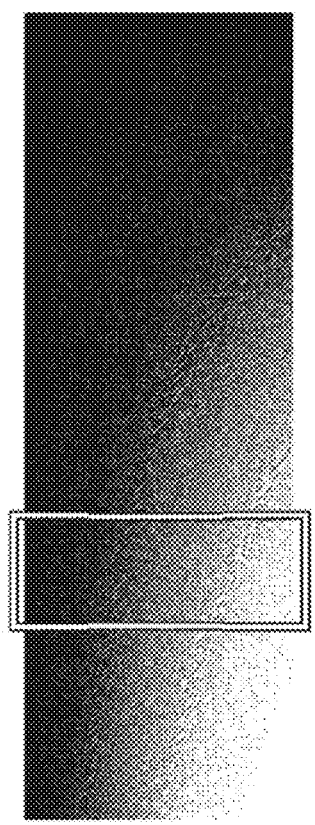
Figure 7D:
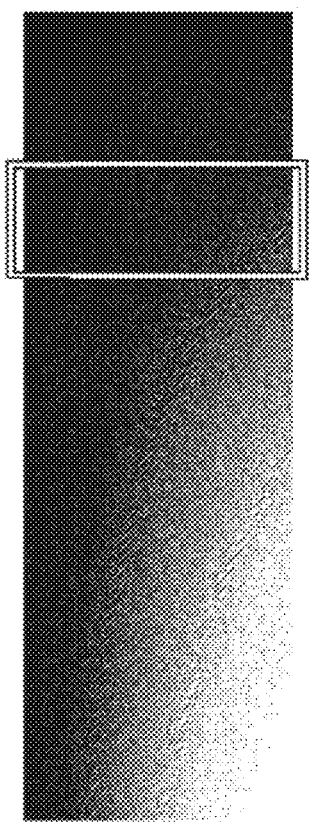
Figure 7E:
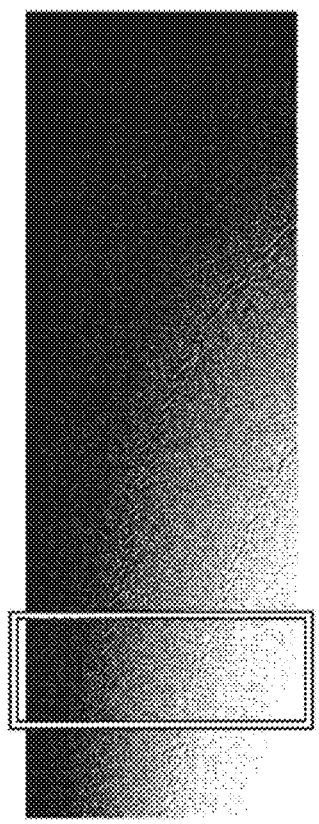
Figure 7F:
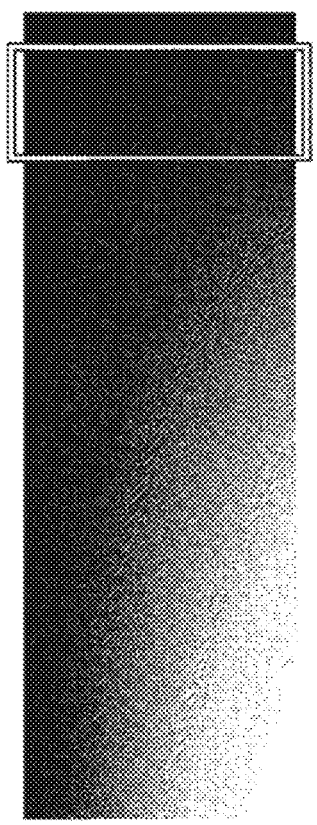
Figure 7G:
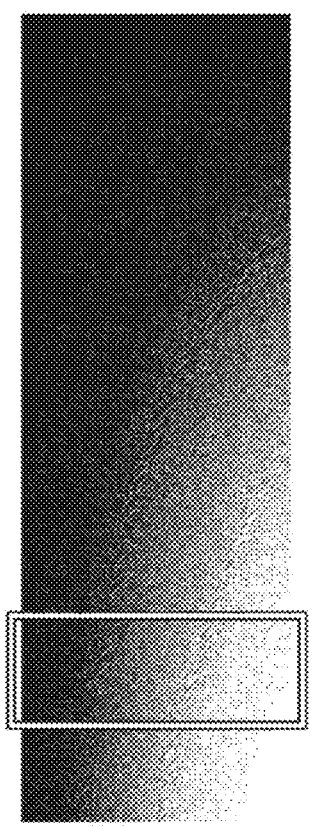
Figure 7H:
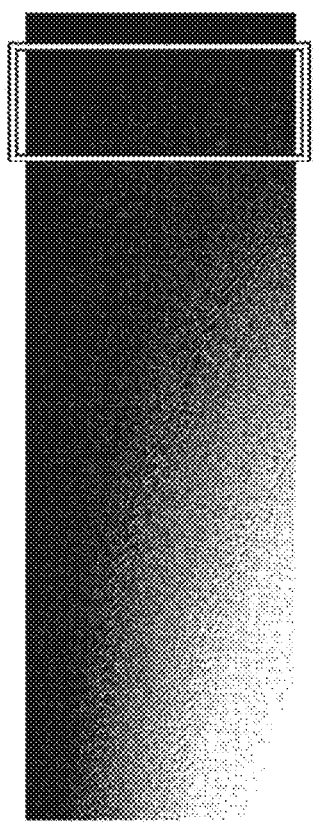
Figure 7I:
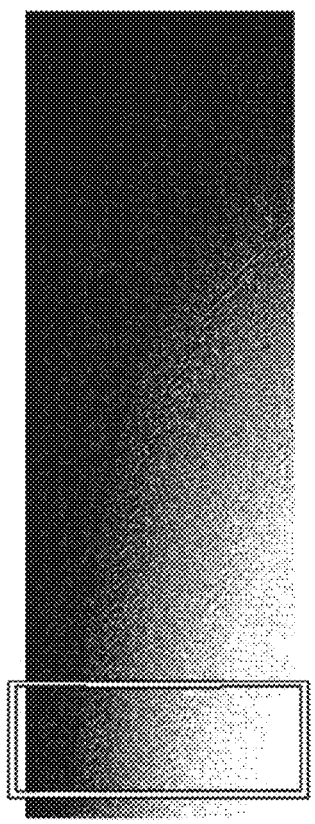

Referring to FIGS. 6A-6I, the mapping regions of the second image corresponding to respective segmentation regions of the first image are shown, with FIG. 6A corresponding to FIG. 7A, FIG. 6B corresponding to FIG. 7B, FIG. 6C corresponding to FIG. 7C, FIG. 6D corresponding to FIG. 7D, FIG. 6E corresponding to FIG. 7E, FIG. 6F corresponding to FIG. 7F, FIG. 6G corresponding to FIG. 7G, FIG. 6H corresponding to FIG. 7H, and FIG. 6I corresponding to FIG. 7I. A part denoted by bold lines in the thickness variable phantom may be the mapping region of the second image corresponding to the segmentation regions of the first image. The mapping region of the second image corresponding to the a respective segmentation region of the first image may be referred to as a calibration phantom region. The first image is mapped to the second image using the calibration phantom.

Since the mapping region of the second image corresponding to a thickness of the object of each segmentation region of the first image is a region but not a line, there may be a difference between the object thickness estimated from the first image and the estimated thickness caused by the presence of abnormal materials.

When deciding or selecting the mapping region of the second image on the basis of a thickness of the object corresponding to each segmentation region of the first image, the mapping region is determined on the basis of data prestored in the storage unit 300 in association with a second image of the thickness variable phantom. That is, from among all regions of the thickness variable phantom, the second image region determiner 430 may decide, select, or determine the region of the second image to be mapped to the first image using per-region data of the second image of the corresponding phantom according to a thickness of the object.

Referring to FIGS. 3 and 4, the image mapper 440 may map each segmentation region of the first image to a region of the second image corresponding to a thickness of the estimated object in operation S130. As described above, the segmentation region of the first image is mapped to a second-image region corresponding to the segmentation region of the first image, and the image mapping will hereinafter be described with reference to FIGS. 8 to 11.

The image mapper 440 may map each one of pixels located at the same position of the segmentation region of the first image to the mapping regions of the second radiation image. The pixels mapped to the overlapped position of the second radiation image are detected on the basis of the mapping result in which pixels located at the same position are mapped to the second radiation image, resulting in formation of the mapping image in operation S140.

Referring to FIG. 3, the image mapper 440 may include a candidate mapping image generator 441, a mapping pixel detector 442, and a mapping image generator 443.

Figure 8:
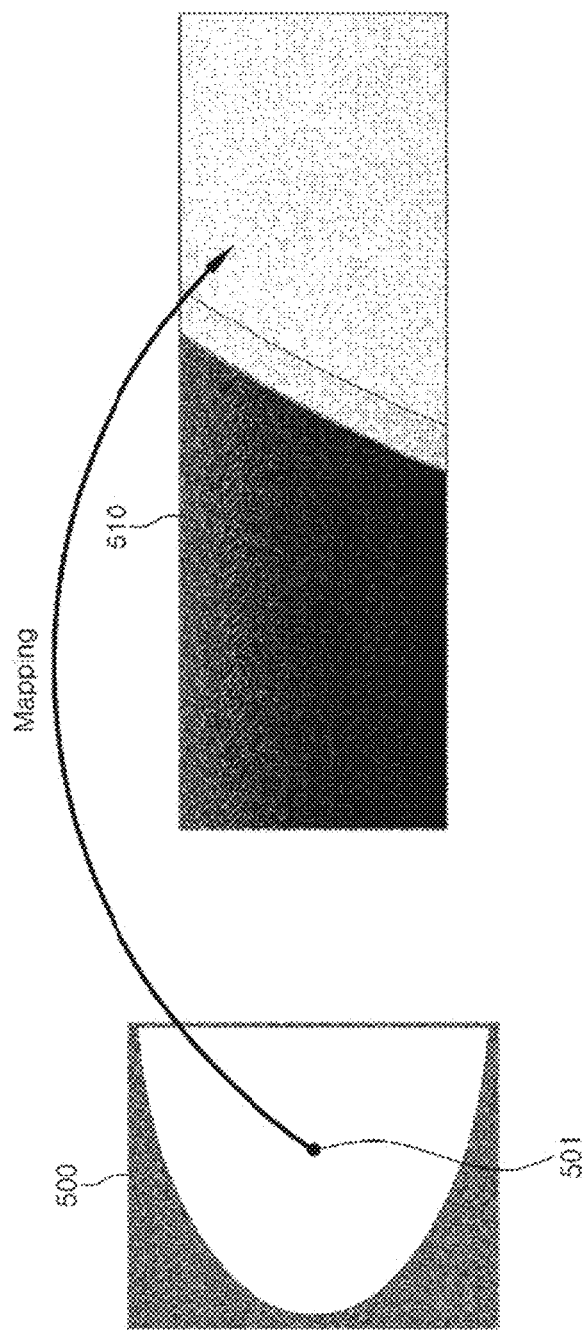
FIG. 8 is a conceptual diagram illustrating an image mapping method according to an exemplary embodiment.

FIG. 8 is a conceptual diagram illustrating an image mapping method according to an exemplary embodiment.

Referring to FIG. 8, one pixel 501 of the first image 500 of the breast tissue may be mapped to the mapping region 510 of the second image decided from the thickness variable phantom. In this case, the first image 500 is mapped on the basis of the intensity of the pixel 501, and is either a high-energy-band radiation image or a low-energy-band radiation image. Although only one first image 500 is shown in FIG. 8, the image mapper 440 may map the pixel 501 located at the same position in each of the high-energy-band radiation image and the low-energy-band radiation image to the mapping region 510 of the second image.

Figure 9A:
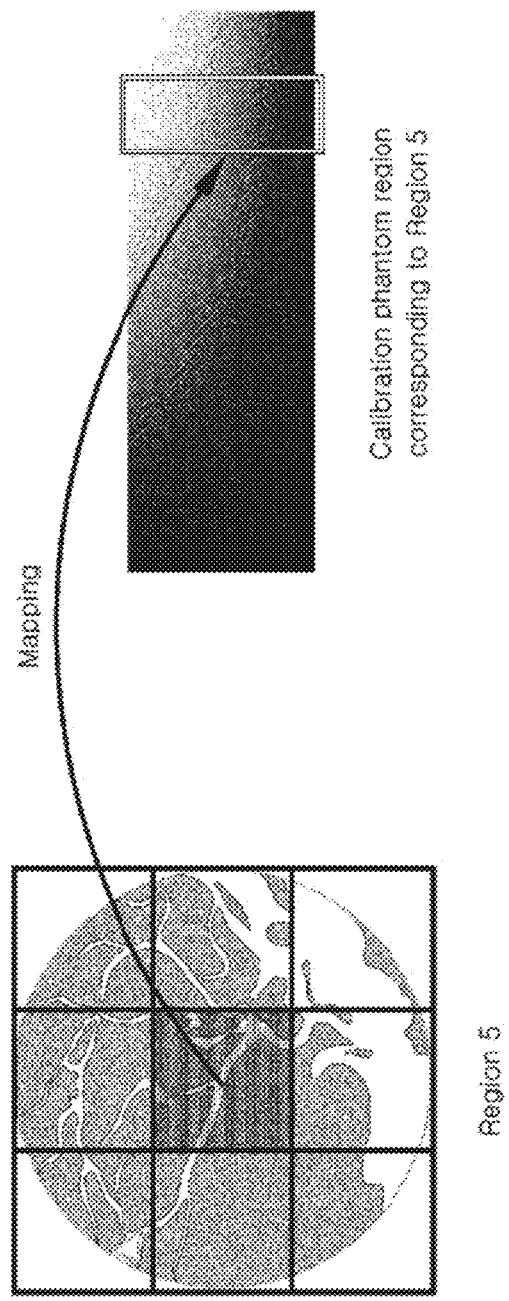
FIGS. 9A-9B are conceptual diagrams illustrating a method for mapping each segmentation region of a first image to a mapping region of a second image according to an exemplary embodiment.
Figure 9B:
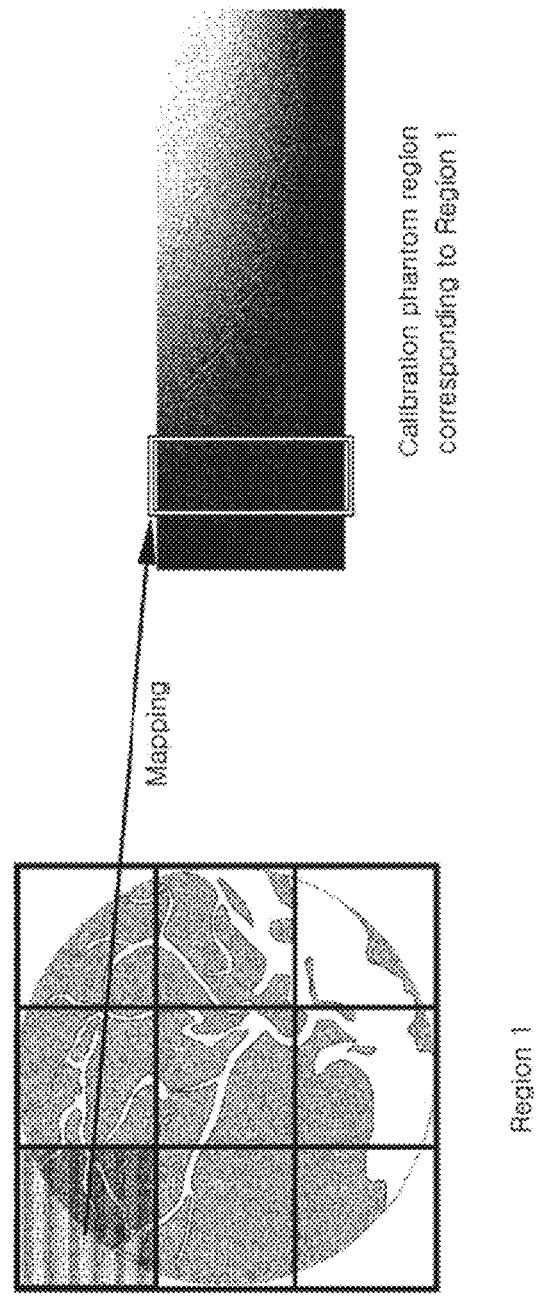

FIGS. 9A-9B are conceptual diagrams illustrating a method for mapping each segmentation region of a first image to a mapping region of a second image according to an exemplary embodiment.

Region 5 of FIG. 6E and Region 1 of FIG. 6A corresponding to segmentation images of the first image may be mapped to the mapping regions of the second image shown in FIG. 7E and FIG. 7A respectively. That is, image mapping to the calibration phantom region of the second image is performed through image data of the second image stored in the storage unit 300 on the basis of the object thickness corresponding to the segmentation region of the first image.

Referring back to FIG. 3, in association with all pixels of each segmentation region of the first images, the candidate mapping image generator 441 may map each of the pixels located at the same position in each segmentation region of the first image to the corresponding calibration phantom region of the second image, so that the corresponding candidate mapping regions are formed. A detailed description thereof will hereinafter be given with reference to FIGS. 10A and 10B.

Figure 10A:
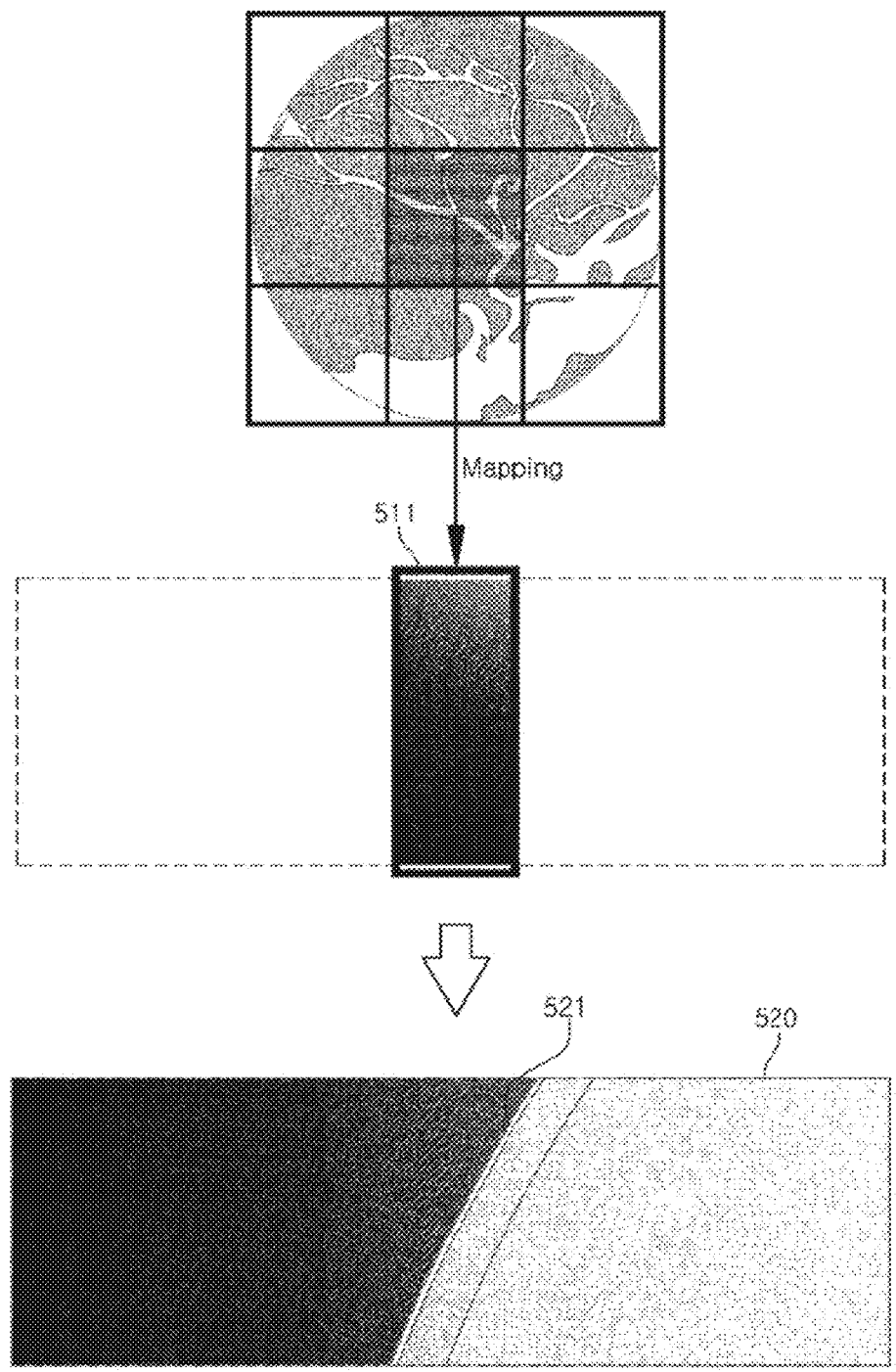
FIG. 10A illustrates a candidate mapping image 520 mapped to a radiation image 520 of a low energy band of a first image to be segmented.

FIG. 10A illustrates a candidate mapping image 520 mapped to a radiation image 520 of a low energy band of a first segmentation image.

Figure 10B:
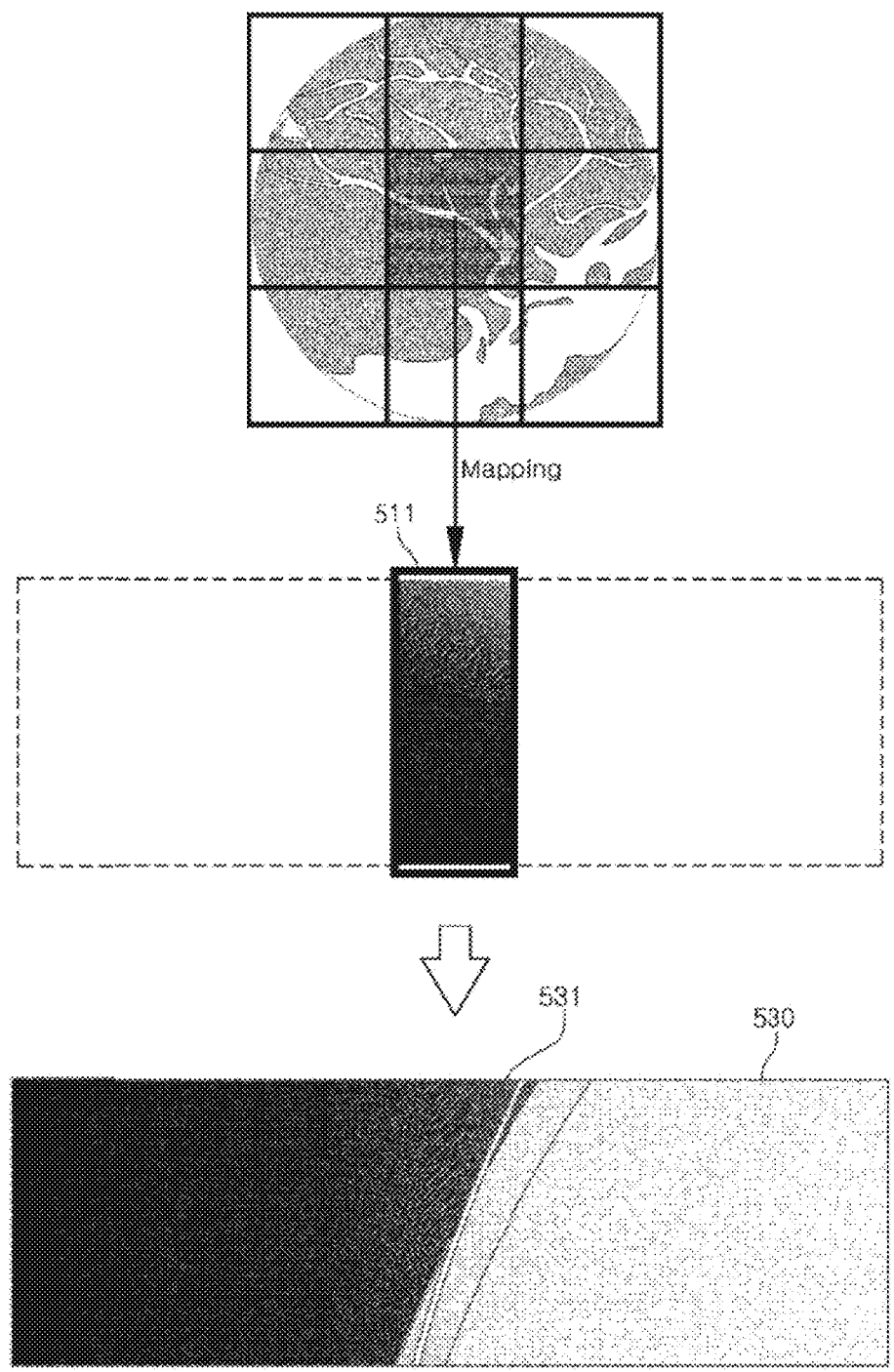
FIG. 10B illustrates a candidate mapping image 530 mapped to a radiation image of a high energy band of a first image to be segmented.

FIG. 10B illustrates a candidate mapping image 530 mapped to a radiation image 530 of a high energy band of a first segmentation image.

Referring to FIG. 10A, the candidate mapping image generator 441 may map any one pixel of the low-energy-band radiation image to the second image. According to the mapping result, the candidate mapping image 520 is generated, on which the line 521 is displayed. In more detail, as shown in FIG. 10A, a low-energy-band radiation image regarding Region 5 of the first image is mapped to the corresponding calibration phantom region 511 of the second image, so that the candidate mapping image 520 indicating the mapping result is formed.

Referring to FIG. 10B, the candidate mapping image generator 441 may map the pixels located at the same position of the high-energy-band radiation image to the second image. Thus, the candidate mapping image generator 441 may generate the candidate mapping image 530 on which the line 531 is displayed.

Respective lines (521, 531) may indicate that a thickness of the breast tissue shown in any pixel of the segmentation region of the first image of each energy band is mapped to the mapping region of the second image decided by the thickness variable phantom. In this case, the thickness of the breast tissue may indicate a thickness of the breast tissue pressed by the mammography.

In this case, the slope of the line 521 of FIG. 10A may be different from the slope of the line 531 of FIG. 10B. Although the same-position pixels indicating the same position of the breast tissues are used, the above pixels are obtained by radiation of different energy bands having different attenuation coefficients. That is, although the pixels are located at the same position, the pixels may have different intensities. Referring back to FIG. 3, the candidate mapping image generator 441 may generate a plurality of candidate mapping images, for example, the candidate mapping image 520 of FIG. 10A and the candidate mapping image 530 of FIG. 10B.

The mapping pixel detector 442 may synthesize the corresponding candidate mapping images to obtain a synthesized image 540, and may detect the pixel mapped to the overlapped position. The corresponding candidate mapping images may be the candidate mapping images of the same-position pixels. For example, the corresponding candidate mapping images may be the candidate mapping image 520 of FIG. 10A and the candidate mapping image 530 of FIG. 10B. The mapping pixel detector 442 will hereinafter be described with reference to FIG. 11.

Figure 11:
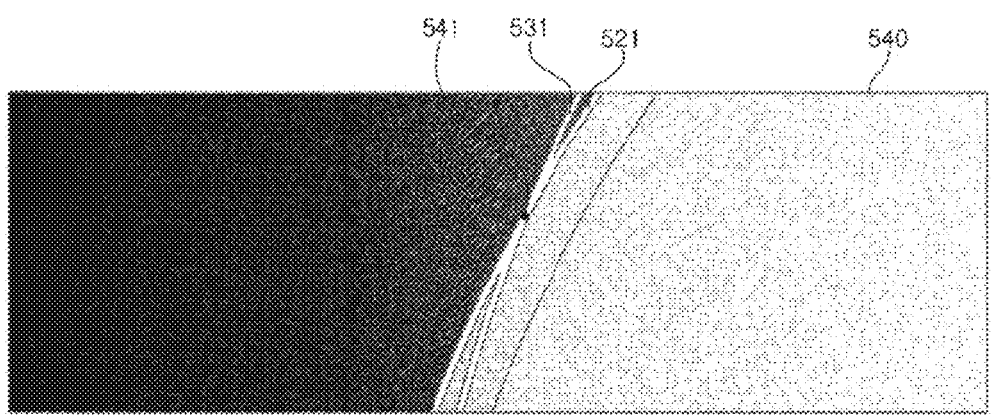
FIG. 11 is a conceptual diagram illustrating a method for allowing a mapping pixel detector to detect a pixel mapped to an overlapped position.

FIG. 11 is a conceptual diagram illustrating a method for allowing the mapping pixel detector 442 to detect a pixel 541 mapped to an overlapping position.

Referring to FIG. 11, a synthesized image 540 is obtained by a combination of the candidate mapping image 520 of FIG. 10A and the candidate mapping image 530 of FIG. 10B. That is, the mapping pixel detector 442 may combine the corresponding candidate mapping images formed by the candidate mapping image generator 441. The synthesized image 540 may include a line 521 displayed on the candidate mapping image 520 of FIG. 10A and a line 531 shown in the candidate mapping region 530 of FIG. 10B. The above-mentioned lines (521, 531) may indicate the mapping result in which the thickness of the breast tissues shown in any pixel of the radiation image of each energy band is mapped to the thickness variable phantom. As previously stated above, a high-energy-band radiation image and a low-energy-band radiation image have been used to estimate the thickness of the breast tissues as shown in Equation 3. That is, as can be seen from Equation 3, thickness values are denoted by $(t_f, t_g)$ and the number of thickness values is set to 2, so that two simultaneous equations are needed to calculate the two thickness values.

Referring to FIG. 11, two simultaneous equations may correspond to respective lines (521, 531) mapped from the radiation images having different energy bands. Therefore, the pixel 541 of a specific position at which the lines (521, 531) of the synthesized image 540 cross each other may correspond to the actual thickness of the breast tissues. In more detail, a thickness denoted by one point of the thickness variable phantom corresponding to the pixel 541 is the actual thickness of the breast tissues.

That is, the mapping pixel detector 442 may detect the pixel 541 mapped to the overlapped position on the basis of the synthesized image 540 obtained by a combination of the candidate mapping images.

The pixel 541 shown in FIG. 11 is mapped to any one pixel of the first segmentation image. The candidate mapping image generator 441 and the mapping pixel detector 442 may generate, synthesize, or create the candidate mapping images of all pixels of the first segmentation image, so that pixels located at the same position, such as the pixel 541 shown in FIG. 11, can be detected.

Referring to FIG. 3, the mapping image generator 443 may display the pixel mapped to the overlap position on the second image, resulting in formation of the mapping image. The mapping image generator 443 may display the mapping pixels corresponding to all pixels of the first segmentation image on the second image segmented into a plurality of regions, resulting in formation of the mapping image.

Figure 12:
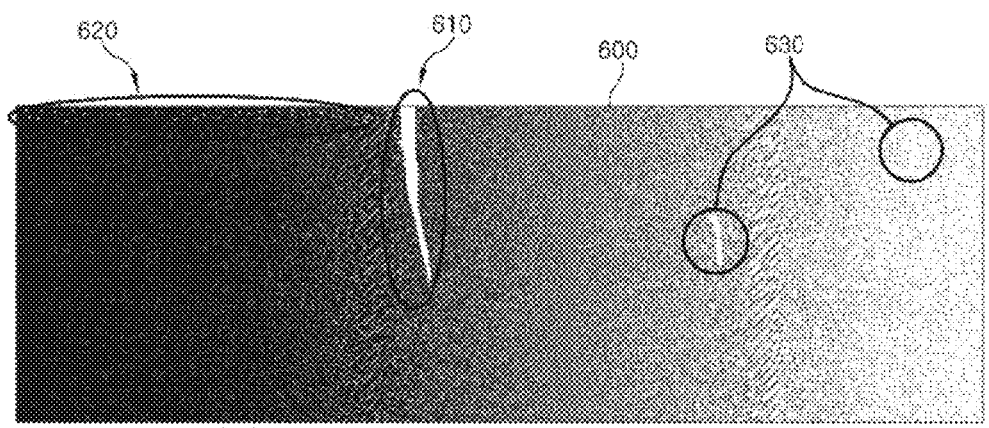
FIG. 12 illustrates a mapping image generated by a mapping image generator according to an exemplary embodiment.

FIG. 12 illustrates a mapping image generated by the mapping image generator according to an exemplary embodiment.

Referring to FIG. 12, the mapping image 600 is generated by the image mapper 440. All the mapping results of respective pixels of the first images are displayed on the mapping image 600. As described above, most breast tissues are composed of normal tissues, so that a reference region 610 in which most mapping pixels are concentrated is present in the mapping region 600. If the abnormal tissue is present in the breast tissues, at least one specific region 630 is present. In addition, when the breast tissues are captured and imaged, the other region 620 may indicate the unpressed breast tissues. This embodiment may mainly use the reference region 610 indicating the pressed breast tissues.

The image analyzer 450 may analyze the reference region corresponding to normal tissues contained in a local region and the specific region corresponding to abnormal tissues contained in the local region on the basis of the formed mapping image in operation S150.

As can be seen from FIG. 3, the detailed structure of the image analyzer 450 includes a reference region estimator 451 and a specific region determiner 452.

In the mapping region, the position of the reference region may indicate a thickness of normal tissues, and the position of the specific region may indicate a thickness of the breast tissues having abnormal tissues. The reason why the reference region and the specific region are located at different positions is that the density, attenuation coefficient, etc. of the breast tissues having only normal tissues are different from those of the abnormal breast tissues having abnormal tissues. That is, the position of the reference region corresponds to the same value as in a total thickness of the breast tissues, and the position of the specific region may correspond to a value different from the thickness of normal tissues.

The reference region estimator 451 may estimate the position of the reference region from the generated mapping image, and the reference-region position can be estimated in various ways. For convenience of description, only some of the methods for estimating the reference-region position will hereinafter be described in detail.

The reference region estimator 451 may estimate the reference region on the basis of the distribution of pixels mapped to the generated mapping image. For example, as can be seen from FIG. 12, the reference region estimator 451 may estimate a region in which the largest number of mapping pixels is concentrated as the reference region 610. In this case, the thickness of normal tissues denoted by the reference region may correspond to a specific pixel located at the highest position of each row of the reference region.

In another example, the reference region estimator 451 may apply the Principal Component Analysis (PCA) or Independent Component Analysis (ICA) algorithm to the intensity of pixels mapped to the generated mapping image, so that the reference region can be estimated using the PCA or ICA algorithm.

The specific region determiner 452 may determine at least one specific region located apart from the reference region in the generated mapping image. In more detail, the specific region determiner 452 may determine the pixel mapped to a position spaced apart from the reference region of the generated mapping image by at least a distance of a threshold value or longer, to be a specific region. Here, the threshold value may be arbitrarily established according to the environments of a user.

For example, as can be seen from FIG. 12, the specific region determiner 452 may determine a specific region in which the mapping pixels are concentrated at a specific position spaced apart from the reference region 610 of the mapping region, to be a specific region 630.

In accordance with one embodiment, a specific region located at a position spaced apart from the reference region of the mapping image is determined to be a specific region. In more detail, assuming that abnormal tissues are present in the breast tissues as described above, the abnormal tissues are mapped to a different position from normal tissues of the mapping image due to a difference in density, attenuation coefficient, etc. Therefore, since the specific region is decided, information indicating which one of pixels of the first image is mapped to a pixel of the specific region can be recognized, and information indicating the position of abnormal tissues in the first image can be recognized.

Referring back to FIG. 3, the emphasized image generator 460 may generate the tissue-emphasized image in which the pixel-position region of the first image mapped to a specific region (that is analyzed simultaneously while having the shape of a local region and is analyzed) is emphasized in operation S160. The intensity of each pixel of the tissue-emphasized image is determined according to whether each pixel of the first radiation image is mapped to the reference region or the specific region. For example, the emphasized image generator 460 may emphasize the abnormal tissues by reducing the intensity of the pixel position of the first image mapped to the reference region of the tissue-emphasized image, or by increasing the intensity of the pixel position of the first image mapped to the specific region.

Figure 13:
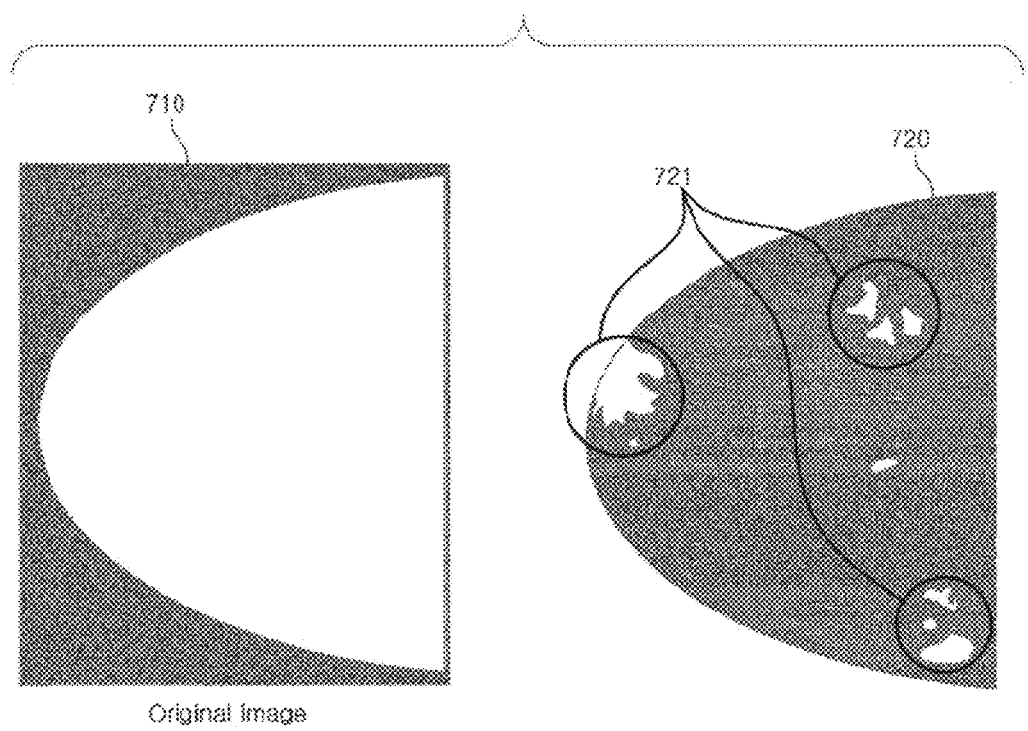
FIG. 13 illustrates an image for emphasizing tissues according to an exemplary embodiment.

FIG. 13 illustrates an image 720 for emphasizing tissues according to an exemplary embodiment.

Referring to FIG. 13, the emphasized image generator 460 may generate the tissue-emphasized image 720 in operation S160. The tissue-emphasized image 720 may have the shape of the breast tissues of the first image 710, and most pixels of the tissue-emphasized image 720 are mapped to the reference region. Most pixels of the tissue-emphasized image 720 have the low intensity and indicate normal tissues. However, the pixels 721 mapped to a specific region of the tissue-emphasized image 720 are emphasized by high intensity, and the pixels 721 may indicate abnormal materials having abnormal tissues.

The X-ray imaging apparatus may generate the tissue-emphasized image 720 shown in FIG. 13, so that more accurate diagnosis information for abnormal tissues contained in the breast tissues can be supplied to the subject and the medical experts. That is, the image processor 400 may generate the tissue-emphasized image in which anatomical structures of respective tissues are clearly shown using characteristics in which organs constructing the human body have different absorption characteristics according to respective energy bands. As a result, the tissue-emphasized image in which anatomical structures of respective tissues are clearly shown can be generated.

The image processor 400 may further include the tissue characteristic estimator 470. The tissue characteristic estimator 470 may estimate the thickness and density of a local region on the basis of the shape and position of the reference region analyzed in the generated mapping image, and may estimate the category of a specific tissue on the basis of the shape and position of the analyzed specific region. In more detail, the tissue characteristic estimator 470 may estimate the component ratio and density of the adipose tissue or the glandular tissue on the basis of the shape and position of the reference region analyzed in the mapping region. If abnormal tissues are large in size, information indicating which kind of materials is used can be estimated according to the position of a specific region in the mapping region.

As described above, according to the above-mentioned embodiment, a first image of the object is segmented into a plurality of segmentation regions, the mapping region of the second image regarding the thickness variable phantom for each segmentation region is determined or selected, and the first segmentation image is mapped to the selected region of the second image so as to generate the mapping image. As described above, the X-ray imaging apparatus and the method for controlling the same have been disclosed to generate the tissue-emphasized image of the part having abnormal materials.

After control completion of the above-mentioned operations, the image synthesizer 480 may combine a segmented part of the first image with a per-region image mapped to the second image in operation S170, resulting in recovery of an original first image.

Figure 14:
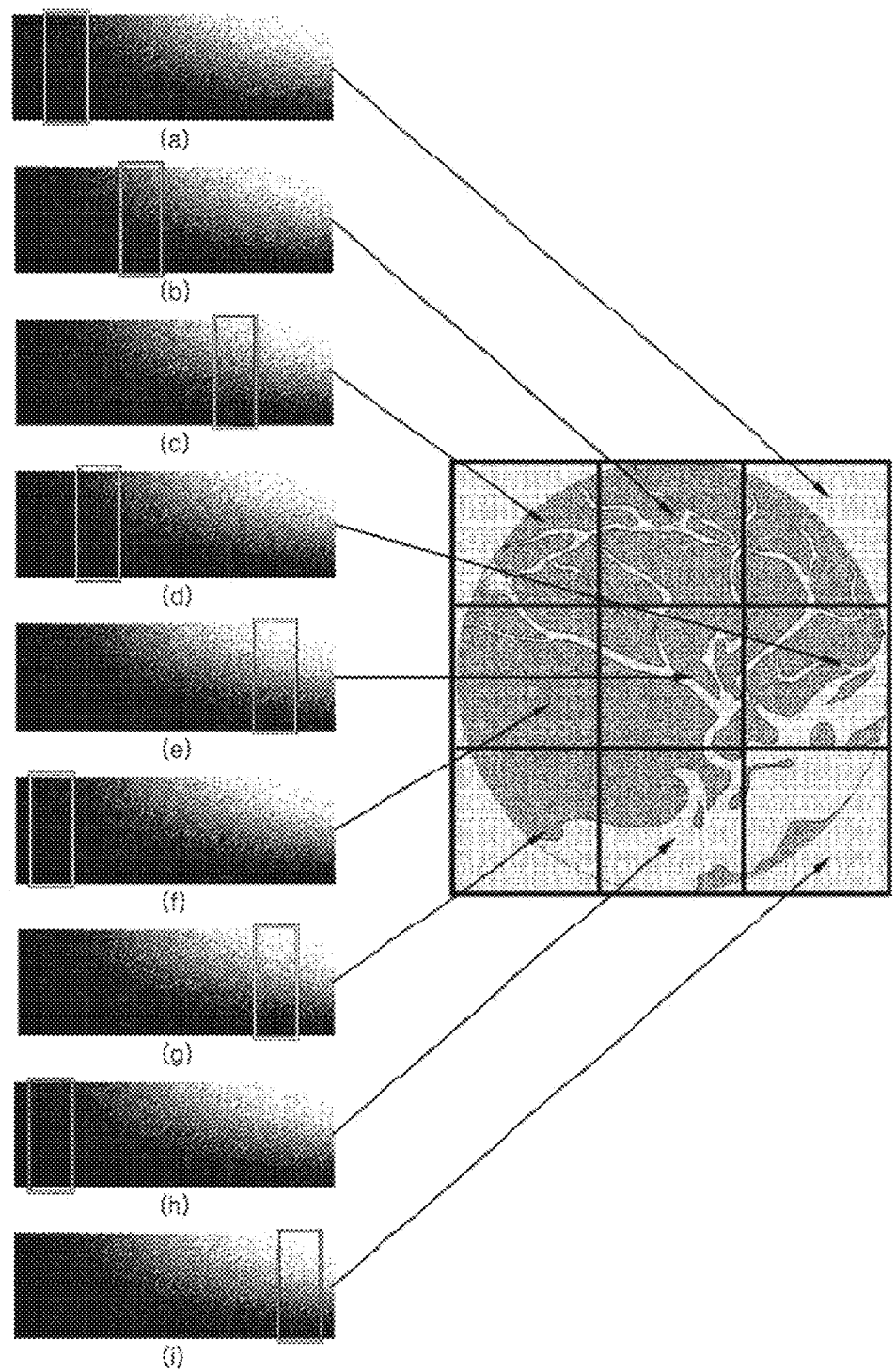
FIG. 14 is a conceptual diagram illustrating a method for re-synthesizing images mapped to a second image corresponding to a segmentation region of a first image according to respective segmentation regions.

FIG. 14 is a conceptual diagram illustrating a method for re-synthesizing images mapped to a second image corresponding to a segmentation region of a first image according to respective segmentation regions.

As shown in FIG. 14, the mapping region of the second image corresponding to each portion of the first segmentation region is combined with the images shown in FIGS. 7A-7I, so that the image obtained when the abnormal material part is displayed on an original image of the first image can be obtained. That is, one region is segmented into 9 regions according to embodiments so that the first image is mapped to the second image. A per-region image for abnormal materials contained in the object of the breast tissues can be generated for each segmentation region. If all the segmentation images are combined, the overall image of the object can be obtained. Therefore, the image combined by the image synthesizer 480 is displayed on the display 132 in operation S180, so that the existing part of abnormal materials contained in the object can be recognized.

The X-ray imaging apparatus and the method for controlling the same according to the exemplary embodiments can segment an X-ray image of the object into a plurality of segmentation images according to respective segmentation regions, can estimate a thickness of the object corresponding to each region, and can perform material isolation, which can mean identifying one or more materials present, for the calibration phantom region corresponding to each region of the object segmented on the basis of the estimated result.

The X-ray imaging apparatus and the method for controlling the same according to the embodiments are not limited thereto, and the above-mentioned embodiments are merely exemplary in all technical aspects.

As is apparent from the above description, the X-ray imaging apparatus and the method for controlling the same according to the embodiments can obtain a precise diagnostic image regarding a target site having an abnormal material. Therefore, doctors or medical experts can more precisely recognize the presence or absence of lesions in an object, the size of a target site having lesions, and the position of the target site having lesions.

Although a few exemplary embodiments have been shown and described, it would be appreciated by those skilled in the art that changes may be made in these embodiments, which are intended to be illustrative, and not to limit the scope of the claims.

What is claimed is:

1. An X-ray imaging apparatus comprising:
   an X-ray detector configured to acquire X-ray data by detecting X-rays; and
   an image processor configured to segment a first image of an object, the first image being generated based on the acquired X-ray data into two or more segmentation regions, to select a region of a second image of a phantom, to identify abnormal materials present in one segmentation region of the two or more segmentation regions based on the selected region, and to generate an image of the object which includes the identified abnormal materials.

2. The X-ray imaging apparatus according to claim 1, wherein the image processor is further configured to estimate a thickness of the object for the one segmentation region of the two or more segmentation regions.

3. The X-ray imaging apparatus according to claim 2, wherein the image processor is further configured to select the region of the second image of the phantom based on the estimated thickness of the object.

4. The X-ray imaging apparatus according to claim 3, wherein the second image comprises a dual energy X-ray image of the phantom.

5. The X-ray imaging apparatus according to claim 3, further comprising:
   a storage unit configured to store data regarding the selected region of the second image corresponding to the thickness of the object.

6. The X-ray imaging apparatus according to claim 3, wherein the image processor is further configured to generate a mapping image that maps the one segmentation region of the first image to the selected region of the second image based on data regarding the selected region of the second image, wherein the data regarding the selected region of the second image is data relating to the estimated thickness of the object.

7. The X-ray imaging apparatus according to claim 6, wherein the image processor is further configured to generate a plurality of mapping images for the two or more segmentation regions of the first image, and to form a recovered image based on the plurality of mapping images.

8. The X-ray imaging apparatus according to claim 1, wherein:
the image processor is further configured to identify the abnormal materials present in the object by displaying the image of the object which includes the identified abnormal materials, and
the identified abnormal materials comprise at least one from among a contrast medium injected into the object or abnormal tissues of the object.

9. The X-ray imaging apparatus according to claim 8, wherein the image processor is further configured to generate an emphasized image which includes an indication of a region of the first image mapped to the contrast medium or the abnormal tissues.

10. The X-ray imaging apparatus according to claim 1, wherein the image processor is further configured to determine a number of the two or more segmentation regions and shapes of the two or more segmentation regions based on the object.

11. The X-ray imaging apparatus according to claim 1, wherein the first image comprises a dual energy X-ray image of the object.

12. A method for controlling an X-ray imaging apparatus comprising:
acquiring X-ray data by detecting X-rays;
segmenting a first image of an object, the first image being generated based on the acquired X-ray data, into two or more segmentation regions,
selecting, a region of a second image of a phantom:
identifying abnormal materials present in one segmentation region of the two or more segmentation regions based on the selected regions; and
generating an image of the object which includes the identified abnormal materials.

13. The method according to claim 12, further comprising:
estimating a thickness of the object for the one segmentation region of the two or more segmentation regions.

14. The method according to claim 13, further comprising:
selecting the region of the second image of the phantom based on the estimated thickness of the object.

15. The method according to claim 14, wherein the second image includes a dual energy X-ray image of the phantom.

16. The method according to claim 14, further comprising:
storing data regarding the selected region of the second image corresponding to the thickness of the object.

17. The method according to claim 14, further comprising:
generating a mapping image that maps the one segmentation region of the first image to the selected region of the second image based on data regarding the selected region of the second image, wherein the data regarding the selected region of the second image is data relating to the estimated thickness of the object.

18. The method according to claim 17, further comprising:
generating a plurality of mapping images for the two or more segmentation regions of the first image, and
forming a recovered image based on the plurality of mapping images.

19. The method according to claim 12, wherein the segmenting of the first image generated into two or more segmentation regions includes:
determining a number of the two or more segmentation regions and shapes of the two or more segmentation regions based on the object.

20. The method according to claim 12, wherein the first image includes a dual energy X-ray image of the object.

* * * * *